US006420531B1

(12) United States Patent
Rubin et al.

(10) Patent No.: US 6,420,531 B1
(45) Date of Patent: Jul. 16, 2002

(54) EPITHELIAL CELL SPECIFIC GROWTH FACTOR, KERATINOCYTE GROWTH FACTOR (KGF)

(75) Inventors: Jeffrey S. Rubin, Rockville; Paul W. Finch, Bethesda, both of MD (US); Stuart A. Aaronson, Great Falls, VA (US)

(73) Assignee: The United States as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/455,620

(22) Filed: May 31, 1995

Related U.S. Application Data

(62) Division of application No. 08/106,775, filed on Aug. 16, 1993, now abandoned, which is a continuation of application No. 07/780,847, filed on Oct. 23, 1991, now abandoned, which is a continuation of application No. 07/304,281, filed on Jan. 31, 1989, now abandoned.

(51) Int. Cl.$^7$ ..................... C07K 14/475; C07K 14/50; C12N 15/18

(52) U.S. Cl. .................. 530/399; 530/395; 930/10; 435/69.4; 435/243; 435/325

(58) Field of Search ............................. 530/350, 399, 530/395; 930/10

(56) References Cited

U.S. PATENT DOCUMENTS

| | | |
|---|---|---|
| 4,444,760 A | 4/1984 | Thomas, Jr. |
| 4,743,679 A | 5/1988 | Cohen et al. |

FOREIGN PATENT DOCUMENTS

| | | |
|---|---|---|
| WO | WO89/08666 | 9/1989 |
| WO | WO 95/01434 | 1/1995 |
| WO | WO87/05332 | 9/1998 |

OTHER PUBLICATIONS

Hennings, Henry et al., "Calcium Regulation of Growth and Differentiation of Mouse Epidermal Cells in Culture", Cell (1980), vol. 19, 245–254, MIT, Cambridge, Massachusetts, USA.

Weissman, Bernard E. et al., "Balb and Kirsten Murine Sarcoma Viruses Alter Growth and Differentiation of EGF–Dependent BALM/c Mouse Epidermal Keratinocyte Lines", Cell (1983), vol. 32, 599–606, MIT, Cambridge, Massachusetts, USA.

Falco, Joseph P. et al., "Interactions of growth factors and retroviral oncogenes with mitogenic signal transduction pathways of Balb/MK keratinocytes", Oncogene (1988), vol. 2, 573–578, The Macmillan Press Ltd., Hampton, England.

Tanswell, A. Keith, "Cellular Interactions in Pulmonary Oxygen Toxicity in Vitro: I. Hyperoxic Induction of Fibroblast Factors which alter growth and lipid metabolism of pulmonary epithelial cells", Experimental Lung Research (1983), vol. 5, 23–26, Research Triangle Park, NC, USA.

James Barrett, Textbook of Immunology "An Introduction to Immunochemistry and Immunobiology," 3rd Edition, 110–113 (1978).

R. Derynck et al., Cell, "Human Transforming Growth Factor–α: Precursor Structure and Expression in E. coli" 38: 287–297 (1984).

F. Esch et al., Proc. Nat'l. Acad. Sci. USA, Primary Structure of Bovine Pituitary Basic Fibroblast Growth Factor (FGF) and Comparison with the Amino–Terminal Sequence of Bovine Brain Acidic FGF, 82: 6507–6511, (1985).

Ron et al., J. Bio. Chem., 268: 2984 (1992).

Rubin, et al., "Purification and Characterization of a Newly Identified Growth Factor Specific for Epithelial Cells," Proc. Natl. Acad. Sci. USA, vol. 86, pp. 802–806 (1989).

Finch, et al., "Human KGF Is FGF–Related with Properties of a Paracrine Effector of Epithelial Cell Growth," Science, vol. 245, pp. 752–755 (1989).

Lewin, Science, 237: 1570 (1987).

Reeck et al., Cell, 50: 667 (1987).

Tsuboi et al., "Recombinant Basic Fibroblast Growth Factor Stimulates Wound Healing–Impaired db/db/ Mice," J. Exp. Med., 172: 245–251 (1990).

Hebda et al., "Basic Fibroblast Growth Factor Stimulation of Epidermal Wound Healing in Pigs," J. Investigative Dermatology, 95: 626 (1990).

Stenberg et al., "Effect of bFGF on the Inhibition of Contraction Caused by Bacteria," Journal of Surgical Research, 50: 47–50 (1991).

"Expression of the FGF–Related Proto–Oncogene Int–2 During Gastrulation and Neurulation in the Mouse," The EMBO Journal, 7: 691–695 (1988).

"Two Proto–Oncogenes Implicated in Mammary Carcinogenesis, Int–1 and Int–2, Are Independently Regulated During Mouse Development," Proc. Natl. Acad. Sci. USA, 83: 7806–7810 (1986).

(List continued on next page.)

Primary Examiner—Christine J. Saoud
(74) Attorney, Agent, or Firm—Heller Ehram White and McAuliffe

(57) ABSTRACT

Discoveries are disclosed that show particular aspects of recombinant DNA technology can be used sucessfully to produce hitherto unknown human keratinocyte growth factor (KGF) protein free of other polypeptides. These proteins can be produced in various functional forms from spontaneously secreting cells or from DNA segments introduced into cells. These forms variously enable biochemical and functional studies of this novel protein as well as production of antibodies. Means are described for determining the level of expression of genes for the KGF protein, for example, by measuring mRNA levels in cells or by measuring antigen secreted in extracellular or body fluids.

44 Claims, 13 Drawing Sheets

OTHER PUBLICATIONS

Gillespie et al., "Mesoderm–Inducing Properties of Int–2 and kFGF: Two Oncogene–Encoded Growth Factors Related to FGF," *Development,* 106: 79–83 (1989).

Moore et al., "Sequence Topography and Protein Coding Potential of Mouse Int–2," *EMBO, J.V.S.,* 5: 919–924 (1986).

Stiles et al., "Reciprocal Autocrine and Paracrine Regulation of Growth of Mesenchymal and Alveolar Epithelial Cells From Fetal Lung," *Experimental Lung Research,* 11: 165–177 (1986).

Chan et al., Epithelial–Stromal Interactions: Specific Stimulation of Corneal Epithelial Cell Growth in Vitro by a Factor(s) From Cultured Stromal Fibroblasts *Exp. Eye Res.,* 36: 231–246 (1983).

James, "Polypeptide Growth Factors: Isolation of Brain Fibroblast Growth Factors by Heparin–Sepharose Affinity".

Gospodarowics et al., "Chromatography: Identity With Pituitary Fibroblast Growth Factor".

"Heparin Binds Endothelial Cell Growth Factor, The Principal Endothelial Cell Mitogen Cell Mitogen in Bovine Brain," *Science,* 225.

Conn et al., "The Isolation and Purification of Two Anionic Endothelial Cell Growth Factors From Human Brain".

Balb and Kirsten Murine Sarcoma Viruses Alter Growth and Differentiation of EGI Dependant Balb/c Mouse Epidermal Keratinocyte Lines.

Aaronson et al., "SV40 T Antigen Induction and Transformation in Human Fibroblast Cell Strains".

Pearson et al., "Improved Tools for Biological Sequence Comparison".

Roberts et al., "Heparin Sulphate Bound Growth Factors: A Mechanism for Stromal Cell Mediated Haemopoiesis".

Gilchrest et al., "Autocrine and Paracrine Growth Stimulation of Cells Derived from Human Skin".

Burges et al., *Annul. Rev. Biochem,* 58 (1989).

Staiano–Coico et al., *J. Exp. Med.,* 178: 865–878 (1993).

Pierce et al., *J. Exp. Med.,* 179: 831 (1994).

Thomason, A., Abstract, Amer. Gastroenter. Assoc. Meeting (Jun. 1994).

Panos, R., Abstract, ATS Intern. Conference, (May 1995).

Ulich et al., *J. Clin. Invest.,* 93: 1298 (1994).

Housley et al., *J. Clin. Invest.,* 94: 001–0014 (1994).

Ulich et al., *Am. J. Path.,* 144: 862 (1994).

Alarid et al., *PNAS (USA)* 91: 1074 (1994).

Koji et al., *J. Cell. Biol.,* 125: 393 (1994).

Koos et al., *J. Steroid Biochem. Molec. Biol.,* 45: 217 (1993).

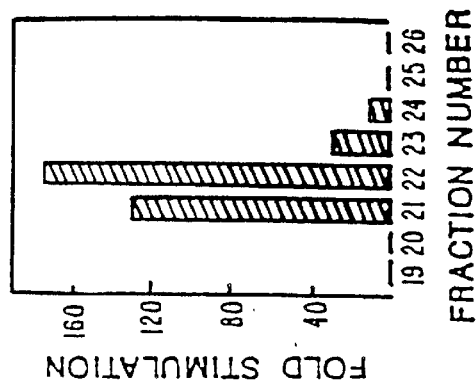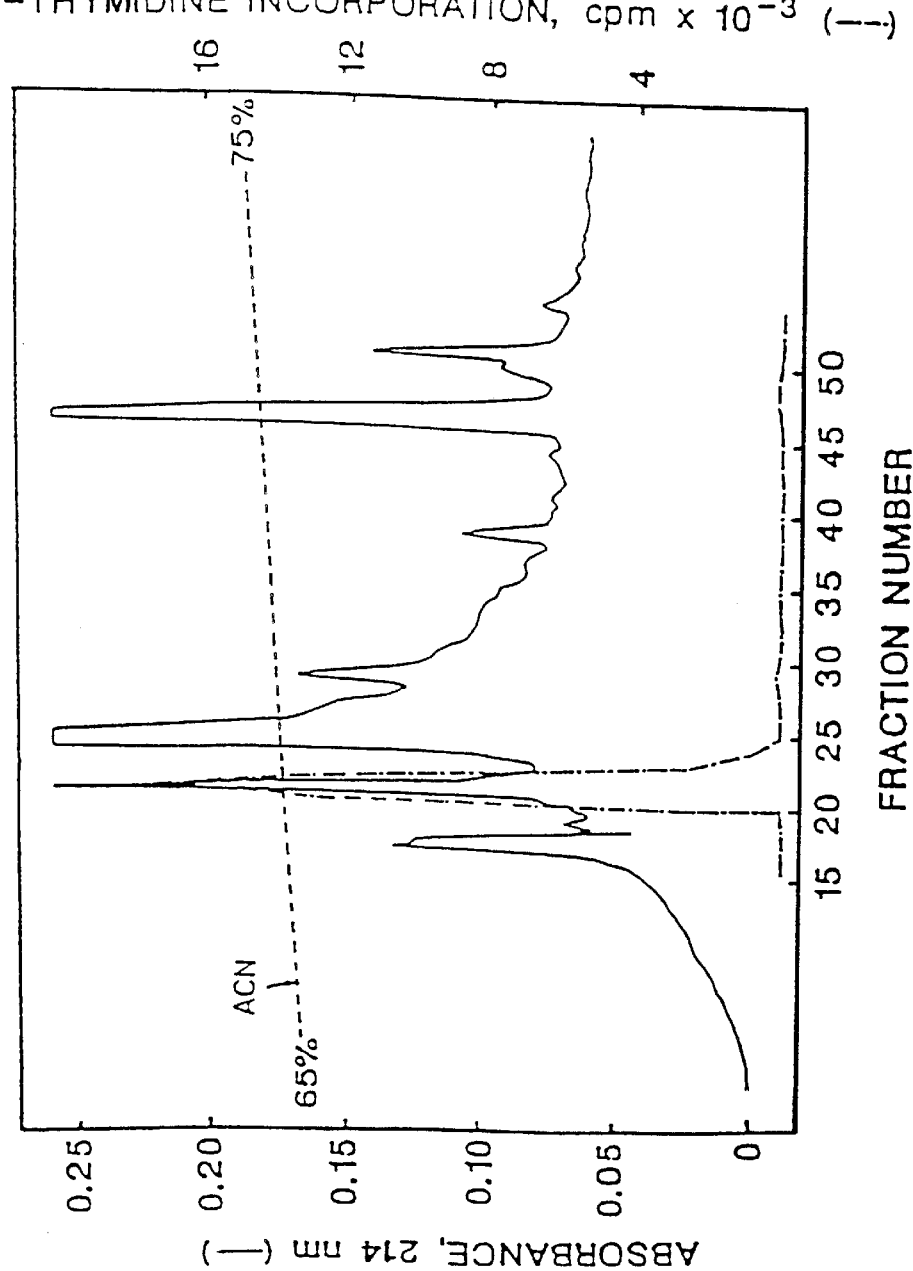

FIG. 5(a) 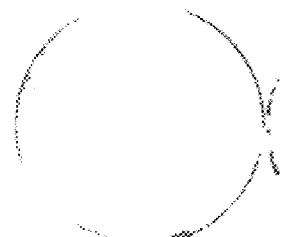 FIG. 5(b) 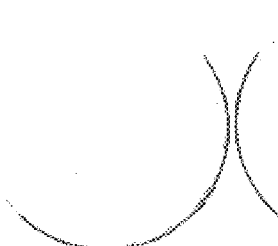 FIG. 5(c) 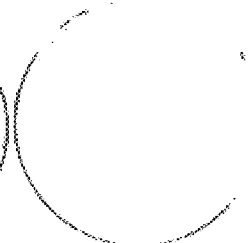 FIG. 5(d) 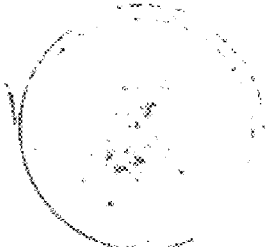
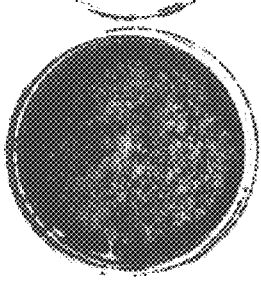 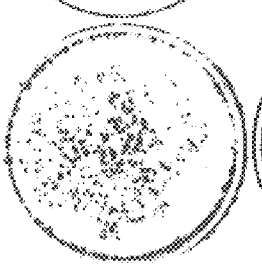 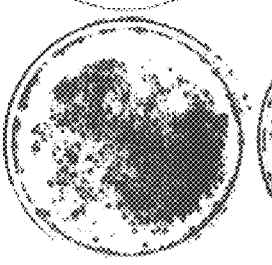 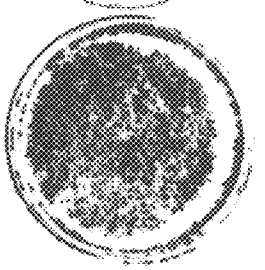
FIG. 5(e)   FIG. 5(f)   FIG. 5(g)   FIG. 5(h)

```
   1 ACGCGCTCACACACAGAGAGAAAATCCTTCTGCCTGTTG
 121 GCACCAGGCAGACAACAGACATGGAATTCTTATATATCC
 241 TTATCAACAGAGTTATTTAAGGAGGAATCCTGTGTTGTT

361 AAGAGGTCAATGACCTAGGAGTAACAATCAACTCAAGAT
```
```
                                     20
         L  L  Y  R  S  C  F  H  I  I  C  L  V
 481 TTTGCTCTACAGATCATGCTTTCACATTATCTGTCTAGT
                                     60
         T  R  S  Y  D  Y  M  E  G  G  D  I  R
 601 CACAAGAAGTTATGATTACATGGAAGGAGGGGATATAAG
                                    100
         N  N  Y  N  I  M  E  I  R  T  V  A  V
 721 GAATAATTACAATATCATGGAAATCAGGACAGTGGCAGT
                                    140
         C  N  E  D  C  N  F  K  E  L  I  L  E
 841 ATGCAATGAAGATTGTAACTTCAAAGAACTAATTCTGGA
                                    180
         P  V  R  G  K  K  T  K  K  E  Q  K  T
 961 TCCTGTAAGAGGAAAAAAAACGAAGAAAGAACAAAAAAC
```
```
1081 TGGACTGTTTCTTTCTTCTCAAAATTTTCTTTCCTTTT
1201 ACACTGCATTAAAGAAAGATTTGAAAAGTATACACAAAA
1321 TAAATTAATTTACCCTTAAGAGTATGTTAGATTTGATTA
1441 GGTATATCAGACCTACAGGCTTCTGGCAGGATTTGTCAG
1561 AATCAGAAAAAAAATTCTCAAAAAAACTATTATGAAAGT
1681 TCAAGTGGAAAGGGTATTGCTAAAAGGATGTTTCCAAAA
1801 CCTCAAAGTAAAATTGAGAAATCTTTAAGTTTTTTTCAA
1921 TTCCTATGGTTACAGCATTAAACTCTATTTTAAGTTGTT
2041 TTTTAATTTTAAAGGAATAACAAAACTGTCTGGCTCAAC
2161 ATAAGAGCCTGAAGCAATGCTTACAATAGATGTCTCACA
2281 ATATAAGTATTTACAGGATTTTAAAGTTAGAATATATTT
2401 TGTTCAAAAGGTGGCAGCACTGAAAGTTGTTTTCCTGTT
2521 CCTACAGATAACAGGATTATTACAAGGATGAATTTCCAC
2641 GTATGCTAACCACTGTGGTTTTAATTTCAAAATATTTGT
2761 CAATAGATTCATTTAATTTTCCTGTGGTTGACCTATACG
2881 CACCTGATTCAAGGACTTTGCTAGCTAGGTTTTGAGGTC
3001 GCAGACTATCTGTTCATAATCAGTTTTCAGTGTGAATTC
3121 TTAAATAGAAATAGTGTATATACATATAAAATACAAGCT
3241 ATTTAGTGGTAAATCCATTCCTGGTAGTATAAGTCACCT
3361 AAATTTGCTCTAGTTACACACCTTTAGAATTCTAGAATA
3481 GCTGGGTAGATATACAGCTGTCACAAGAGTCTAGATCAG
3601 AGATATAGCCTTTACATTTGTACACAAATGTGACTATGT
3721 TCAATTCTGATTCCTATTCACCTTTTGTTTATGAATGGA
3841 TCTAACAATTAGAAAAAAAAAAAAAAAAAAAAAAAAAA
```

| FIG. 7A | | FIG. 7C |

```
ATTTATGGAAACAATTATGATTCTGCTGGAGAACTTTT
AGCTGTTAGCAACAAAACAAAAGTCAAATAGCAAACAG
ATCAGGAACTAAAAGGATAAGGCTAACAATTTGGAAAG

TCATTTTCATTATGTTATTCATGAACACCCGGAGCACT
                  30
       G  T  I  S  L  A  C  N  D  M  T  P
GGGTACTATATCTTTAGCTTGCAATGACATGACTCCAG
               70
   V  R  R  L  F  C  R  T  Q  W  Y  L
AGTGAGAAGACTCTTCTGTCGAACACAGTGGTACCTGA
               110
       G  I  V  A  I  K  G  V  E  S  E  F
TGGAATTGTGGCAATCAAAGGGGTGGAAAGTGAATTCT
               150
     N  H  Y  N  T  Y  A  S  A  K  W  T
AAACCATTACAACACATATGCATCAGCTAAATGGACAC
               190
     A  H  F  L  P  M  A  I  T  *
AGCCCACTTTCTTCCTATGGCAATAACTTAATTGCATA

ATTTTTTAGTAATCAAGAAAGGCTGGAAAAACTACTGA
ATCAGATTTAGTAACTAAAGGTTGTAAAAAATTGTAAA
TCTGATAATGATTATTTAAATATTCCTATCTGCTTATA
ATAATCAAGCCACACTAACTATGGAAAATGAGCAGCAT
CAATAAAATAGATAATTTAACAAAAGTACAGGATTAGA
ATCTTGTATATAAGATAGCAACAGTGATTGATGATAAT
GTAACATAATCTATCTTTGTATAATTCATATTTGGGAA
TTTGAACTTTATTGTTTTGTTATTTAAGTTTATGTTAT
GGCAAGTTTCCCTCCCTTTTCTGACTGACACTAAGTCT
CAGAACAATACAAATATGTAAAAACTCTTTCACCACAT
GAATGCATGGGTAGAAAATATCATATTTTAAAACTATG
AGATGGCAAGAGCACAATGCCCAAAATAGAAGATGCAG
TTCAAAAGTCTTTCATTGGCAGATCTTGGTAGCACTTT
CATTCAAGTCCCTTTACATAAATAGTATTTGGTAATAC
ACCAGGATGTAGAAAACTAGAAAGAACTGCCCTTCCTC
AGGCTTCAGTAACTGTAGTCTTGTGAGCATATTGAGGG
ACTGAATGTTTATAGACAAAAGAAAATACACACTAAAA
ATGTTAGGACCAAATGCTCTTTGTCTATGGAGTTATAC
AAAAAAGACTTCTAGAAATATGTACTTTAATTATTTGT
TTAAAACTGTAAGGGGCCTCCATCCCTCTTACTCATTT
TTAGCACATGCTTTCTACTCTTCGATTATTAGTATTAT
CTTGGCAATGCACTTCATACACAATGACTAATCTATAC
AAGCTTTGTGCAAAATATACATATAAGCAGAGTAAGCC
```

| FIG. 7A | | FIG. 7C |

FIG. 7C

| FIG. 7B

```
CAGCTGAGAAATAGTTTGTAGCTACAGTAGAAAGGCTCAAGTT
CGTCACAGCAACTGAACTTACTACGAACTGTTTTTATGAGGAT
AGCAAGTACTCTTTCTTAAATCAATCTACAATTCACAGATAGG
```

```
                                          10
          M  H  K  W  I  L  T  W  I  L  P  T
ACACTATAATGCACAAATGGATACTCACATGGATCCTGCCAAC 40                                  50
 E  Q  M  A  T  N  V  N  C  S  S  P  E  R  H
AGCAAATGGCTACAAATGTGAACTGTTCCAGCCCTGAGCGACA 80                                  90
 R  I  D  K  R  G  K  V  K  G  T  Q  E  M  K
GGATCGATAAAAGAGGCAAAGTAAAAGGGACCCAAGAGATGAA 120                                 130
 Y  L  A  M  N  K  E  G  K  L  Y  A  K  K  E
ATCTTGCAATGAACAAGGAAGGAAAACTCTATGCAAAGAAAGA 160                                 170
 H  N  G  G  E  M  F  V  A  L  N  Q  K  G  I
ACAACGGAGGGGAAATGTTTGTTGCCTTAAATCAAAAGGGGAT
```

```
TGGTATATAAGAACCCAGTTCCAGCAGGGAGATTTCTTTAAG
AAAACTGATCAAGCTGGACTTGTGCATTTATGTTTGTTTTAAG
ACTGGTTGTACAATCATGATGTTAGTAACAGTAATTTTTTTCT
AAATGGCTGCTATAATAATAATAATACAGATGTTGTTATATAA
TTTAAATGCTTTCTAGTGAAAAATTATAATCTACTTAAACTCT
ACATGCTTATACCTATAAATAAGAACAAAATTTCTAATGCTGC
ACTGTACTTCATCTTACTTGCCACAAAATAACATTTTATAAAT
TATGGCTTTTAATAATGTTCTTCCACAAATAATCATGCTTTT
TTATAAAAAAAAACCTTAATAAGCTGTATCTGTTTCATATGC
AGCACACAGCACTTGGGCCAGCAAATCCTGGAAGCAGACAAAA
ATTCTTGCCAATTAATTGGATCATATAAGTAAAATCATTACAA
TATATTTAAATTTAGTAATTTTCTAATCTCTAGAAATCTCTGC
TTAAGAATAAGGGGCCCTGAATGTCATGAAGGCTTGAGGTCAG
ATATGTTCACCAATGGGAGGTCAATATTTATCTAATTTAAAAG
ATTTATAGATGAGAGTTATATGAAAAGGCTAGGTCAACAAAAA
AGATATACTCTTGGGAGAGAGCATGAATGGTATTCTGAACTAT
CAGAGGAGGACTTAGTTTTCATATGTGTTTCCTTAGTGCCTA
CTAATCTTCATTTTAAAAGGGTAAAACATGACTATACAGAAAT
TTCCATCAAATTACATAGCAATGCTGAATTAGGCAAAACCAAC
TTTTCTCCTATTTTTAAATTTATTATGCAAATTTTAGAAAATA
GTAGTCTAGGAAATTGAGATTTTGATACACCTAAGGTCACGCA
TAGCTAATGGTCTTTGGCATGTTTTTGTTTTTTATTTCTGTTG
TGTGATGATTTGACTCAAAAGGAGAAAAGAAATTATGTAGTTT
TTTTAAAAAATGTTCTTTGAAAGATAAAATTAAATACATGAGTT
```

| FIG. 7B

EPITHELIAL CELL SPECIFIC GROWTH FACTOR, KERATINOCYTE GROWTH FACTOR (KGF)

This application is a divisional application of application Ser. No. 08/106,775, filed Aug. 16, 1993, abandoned, which is a continuation application of Ser. No. 07/780,847, filed Oct. 23, 1991, abandoned, which is a continuation application of Ser. No. 07/304,281, filed Jan. 31, 1989, abandoned.

FIELD OF THE INVENTION

The present invention relates to growth factors, particularly to isolation of a polypeptide growth factor similar to a family of factors including known fibroblast growth factors (FGFs). This invention also relates to construction of complementary DNA (cDNA) segments from messenger RNA (mRNA) encoding the novel growth factor. Further, this invention pertains to synthesis of products of such DNA segments by recombinant cells, and to the manufacture and use of certain other novel products enabled by the identification and cloning of DNAs encoding this growth factor.

ABBREVIATIONS USED IN THIS APPLICATION

| | |
|---|---|
| aFGF | acidic fibroblast growth factor |
| bFGF | basic fibroblast growth factor |
| EGF | epidermal growth factor |
| HSAC | heparin-Sepharose affinity chromatography |
| kb | kilobases |
| kDa | kilodaltons |
| KGF | keratinocyte growth factor |
| NaDodSO$_4$/PAGE | Sodium dodecylsulphate (SDS)/polyacrylamide gel electrophoresis |
| RP-HPLC | reversed-phase high performance liquid chromatography |
| TGFα | transforming growth factor α |

BACKGROUND OF THE INVENTION

Growth factors are important mediators of intercellular communication. These potent molecules are generally released by one cell type and act to influence proliferation of other cell types (James, R. and Bradshaw, R. A. (1984), *Ann. Rev. Biochem.* 53, 259–292). Interest in growth factors has been heightened by evidence of their potential involvement in neoplasia (Sporn, M. B. and Todaro, G. J. (1980), *N. Eng. J. Med.* 303, 878–880). The v-sis transforming gene of simian sarcoma virus encodes a protein that is homologous to the B chain of platelet-derived growth factor (James, R. and Bradshaw, R. A. (1984) *Ann. Rev. Biochem.* 53, 259–292; Doolittle, R. F., et al. (1983) *Science* 221, 275–277). Moreover, a number of oncogenes are homologous of genes encoding growth factor receptors (James, R. and Bradshaw, R. A. (1984) *Ann. Rev. Biochem.* 53, 259–292). Thus, increased understanding of growth factors and their receptor-mediated signal transduction pathways is likely to provide insights into mechanisms of both normal and malignant cell growth.

One known family of growth factors affecting connective tissue cells includes acidic fibroblast growth factor (aFGF), basic fibroblast growth factor (bFGF), and the related products of the hst, and int-2 oncogenes.

Further, it is known that some growth factors, including the following, have heparin-binding properties: aFGF (Maciag, T., Mehlman, T., Friesel, R. and Schreiber, A. B. (1984) *Science* 225, 932–935; Conn, G and Hatcher, V. B. (1984) *Biochem. Biophys. Res. Comm.* 124, 262–268); bFGF (Gospodarowicz, D., Cheng, J., Lui, G. -M., Baird, A. and Bohlen, P. (1984) *Proc. Natl. Acad. Sci. USA* 81, 6963–6967; Maciag, T., Mehlman, T., Friesel, R. and Schreiber, A. B. (1984) *Science* 225, 932–935); granulocyte/machrophage colony stimulating factor (James, R. and Bradshaw, R. A. (1984) *Ann. Rev. Biochem.* 53, 259–292); and interleukin 3 (James, R. and Bradshaw, R. A. (1984) *Ann. Rev. Biochem.* 53, 259–292). Each of these polypeptide factors is produced by stromal cells (James, R. and Bradshaw, R. A. (1984) *Ann. Rev. Biochem.* 53, 259–292, Doolittle, R. F., Hunkapiller, M. W., Hood, L. E., Devare, S. G., Robbins, K. C., Aaronson, S. A. and Antoniades, M. N. (1983) *Science* 221, 275–277, Roberts, R., Gallagher J., Spooncer, E., Allen, T. D., Bloomfield, F. and Dexter, T. M. (1988) *Nature* 332, 376–378). Such factors appear to be deposited in the extracellular matrix, or on proteoglycans coating the stromal cell surface (James, R. and Bradshaw, R. A. (1984) *Ann. Rev. Biochem.* 53, 259–292, Roberts, R., Gallagher, J., Spooncer, E., Allen, T. D., Bloomfield, F. and Dexter, T. M. (1988) *Nature* 332, 376–378). It has been postulated that their storage, release and contact with specific target cells are regulated by this interaction (Roberts, R., Gallagher, J., Spooncer, E., Allen, T. D., Bloomfield, F. and Dexter, T. M. (1988) *Nature* 332, 376–378, Vlodavsky, I., Folkman, J., Sullivan, R., Fridman, R., Ishai-Michaeli, R., Sasse, J. and Klagsburn, M. (1987) *Proc. Natl. Acad. Sci. USA* 84, 2292–2296).

It is widely recognized, however, that the vast majority of human malignancies are derived from epithelial tissues (Wright, N. and Allison, M. (1984) *The Biology of Epithelial Cell Populations* (Oxford University Press, New York) Vol. 1, pp. 3–5). Effectors of epithelial cell proliferation derived from mesenchymal tissues have been described (James, R. and Bradshaw, R. A. (1984) *Ann. Rev. Biochem.* 53, 259–292, Doolittle, R. F., Hunkapiller, M. W., Hood, L. E., Devare, S. G., Robbins, K. C., Aaronson, S. A. and Antoniades, M. N. (1983) *Science* 221, 275–2772, Waterfield, M. D., Scrace, G. J., Whittle, N., Strooband, P., Johnson, A., Wasteton, A., Westermark, B., Heldin, C. -H., Huang, J. S. and Deuel, T. F. (1983) *Nature* 304, 35–39), however, their molecular identities and structures have not been elucidated.

In light of this dearth of knowledge about such mesenchymal growth factors affecting epithelial cells, it is apparent that there has been a need for methods and compositions and bioassays which would provide an improved knowledge and analysis of mechanisms of regulation of epithelial cell proliferation, and, ultimately, a need for novel diagnostics and therapies based on the factors involved therein.

This invention contemplates the application of methods of protein isolation and recombinant DNA technologies to fulfill such needs and to develop means for producing protein factors of mesenchymal origin, which appear to be related to epithelial cell proliferation processes and which could not be produced otherwise. This invention also contemplates the application of the molecular mechanisms of these factors related to epithelial cell growth processes.

SUMMARY OF THE INVENTION

The present invention relates to developments of protein isolation and recombinant DNA technologies, which include production of novel growth factor proteins affecting epithelial cells, free of other peptide factors. Novel DNA segments and bioassay methods are also included.

The present invention in particular relates to a novel protein having structural and/or functional characteristics of a known family of growth factors which includes acidic fibroblast growth factor (aFGF), basic fibroblast growth factor (bFGF) and the related products of the hst, and int-2 oncogenes. This new member of the FGF polypeptide family retains the heparin-binding properties of the FGFs but has evolved a unique target cell specificity. This growth factor appears to be specific for epithelial cells and is particularly active on keratinocytes. Therefore, this novel factor has been designated "keratinocyte growth factor" (KGF). Notwithstanding its lack of activity on fibroblasts, since it is the sixth known member of the FGF polypeptide family, KGF may also be referred to as FGF-6.

Accordingly, this invention relates, in part, to purified KGF or KGF-like proteins and methods for preparing these proteins. Such purified factors may be made by cultivation of human cells which naturally secrete these proteins and application of isolation methods according to the practice of this invention. These proteins can be used for biochemical and biological studies leading, for example, to isolation of DNA segments encoding KGF or KGF-like polypeptides.

The present invention also relates to such DNA segments which encode KGF or KGF-like proteins. In a principal embodiment, the present invention relates to DNA segments, which encode KGF-related products, consisting of: human cDNA clones 32 or 49, derived from polyadenylated RNA extracted from the human embryonic lung fibroblast cell line M426; recombinants and mutants of these clones; and related DNA segments which can be detected by hybridization to any of the above human DNA segments, which relates segments encode KGF-like proteins or portions thereof.

In the practice of one embodiment of this invention, the DNA segments of the invention are capable of being expressed in suitable host cells, thereby producing KGF of KGF-like proteins. The invention also relates to m-RNAs produced as the result of transcription of the sense strands of the DNA segments of this invention.

In another embodiment, the invention relates to a recombinant DNA molecule comprising a vector and a DNA of the present invention. These recombinant molecules are exemplified by molecules comprising a KGF cDNA and any of the following vector DNAs: a bacteriophage λ cloning vector (exemplified by λpCEV9); a DNA sequencing plasmid vector (e.g., a pUC variant); a bacterial gene expression vector (e.g., pKK233-2); or a mammalian gene expression vector (such as pMMT).

In still another embodiment, the invention comprises a cell, preferably a mammalian cell, transformed with a DNA of the invention. Further, the invention comprises cells, including insect cells, yeast cells and bacterial cells such as those of *Escherichia coli* and *B. subtilis*, transformed with DNAs of the invention. According to another embodiment of this aspect of the invention, the transforming DNA is capable of being expressed in the cell, thereby increasing in the cell the amount of KGF or KGF-like protein encoded by this DNA.

The primary KGF translation product predicted from its cDNA sequence contains an N-terminal hydrophobic region which likely serves as a signal sequence for secretion and which is not present in the mature KGF molecule. In a most preferred embodiment of the gene expression aspect of the invention, the cell transformed by the DNA of the invention secretes the protein encoded by that DNA in the (truncated) form that is secreted by human embryonic lung fibroblast cells.

Still further, this invention contemplates KGF or KGF-like proteins produced by expression of a DNA of the invention, or by translation of an RNA of the invention. Preferably, these proteins will be of the secreted form (i.e., lacking an apparent signal sequence). These protein factors can be used for functional studies, and can be purified for additional structural and functional analyses, such as qualitative and quantitative receptor binding assays.

Moreover, the ability to produce large quantities of this novel growth factor by recombinant techniques will allow testing of its clinical applicability in situations where specific stimulation of growth of epithelial cells is of particular importance. Accordingly, this invention includes pharmaceutical compositions comprising KGF or KGF-like polypeptides for use in the treatment of such conditions, including, for example, healing of wounds due to burns, or stimulation of transplanted corneal tissue.

According to this embodiment of the invention, the novel KGF-like proteins will be protein products of "unmodified" DNAs and mRNAs of the invention, or will be modified or genetically engineered protein products. As a result of engineered mutations in the DNA sequences modified KGF-like proteins will have one or more differences in amino acid sequence from the corresponding naturally occurring "wild-type" proteins. According to one embodiment of this aspect of this invention, the modified KGF-like proteins will include "chimeric" molecules comprising segments of amino acid sequences of KGF and at least one other member of the FGF peptide family.

Ultimately, given results of analogous successful approaches with other peptide factors having similar properties, development of such chimeric KGF-like polypeptides should lead to superior, "second generation" forms of KGF-like peptides for clinical purposes. These modified KGF-like products might be smaller, more stable, more potent, and/or easier or less expensive to produce, for example.

This invention further comprises novel bioassay methods for determining expression in human cells of the mRNAs and proteins produced from the genes related to DNA segments of the invention. According to one such embodiment, DNAs of this invention may be used as probes to determine steady state levels or kinetics of induction of related mRNAs. The availability of the KGF-related cDNA clones makes it possible to determine whether abnormal expression of this growth factor is involved in clinical conditions characterized by excessive epithelial cell growth, including dysplasia and neoplasia (e.g., psoriasis or malignant or benign epithelial tumors).

This invention also contemplates novel antibodies made against a peptide encoded by a DNA segment of the invention. In this embodiment of the invention, the antibodies are monoclonal or polyclonal in origin, and are generated using KGF-related polypeptides from natural, recombinant or synthetic chemistry sources.

The antibodies of this invention bind specifically to KGF or a KGF-like protein which includes the sequence of such peptide, preferably when that protein is in its native (biologically active) conformation. These antibodies can be used for detection or purification of the KGF or KGF-like protein factors. In a most preferred embodiment of this aspect of the invention, the antibodies will neutralize the growth promoting activity of KGF, thereby enabling mechanistic studies and, ultimately, therapy for clinical conditions involving excessive levels of KGF.

BRIEF DESCRIPTION OF THE DRAWINGS

FIGS. 2A, 2B, and 2C illustrates results of further purification of the mitogen from human fibroblasts using HPLC with an adsorptive matrix. Panel (A) shows the profile on Reversed-phase $C_4$HPLC of BALB/MK mitogenic activity. Active fractions eluted from heparin-Sepharose with 0.6M NaCl were processed with the Centricon –10 and loaded directly onto a $C_4$ Vydac column (4.6×250 mm) which had been equilibrated in 0.1% trifluoroacetic acid/20% acetonitrile (ACN). After washing the column with 4 ml of equilibration buffer, the sample was eluted with a modified linear gradient of increasing % ACN. Fraction size was 0.2 ml and flow rate was 0.5 ml/min. Aliquots for the assay of $^3$H-thymidine incorporation in BALB/MK cells were promptly diluted 10-fold with 50 $\mu$g/ml bovine serum albumin/20 mM Tris-HCl, pH 7.5, and tested at a final dilution of 200-fold. (B) NaDodSO$_4$/PAGE analysis of selected fractions from the $C_4$ chromatography shown in-panel A. Half of each fraction was dried, redissolved in NaDodSO$_4$/2mercaptoethanol, heat denatured and electrophoresed in a 14% polyacrylamide gel which was subsequently stained with silver. The position of each molecular weight marker (mass in kDa) is indicated by an arrow. (C) DNA synthesis in BALB/MK cells triggered by the fractions analyzed in Panel B. Activity is expressed as the fold stimulation over background which was 100 cpm.

FIG. 5 shows comparative growth of BALB/MK cells in a chemically defined medium in response to different combinations of growth factors. Cultures were plated at a density of $2.5\times10^4$ cells per dish on 35 mm Petri dishes precoated with poly-D-lysine/fibronectin in a 1:1 mixture of Eagle's minimal essential medium and Ham's F12 medium supplemented with transferrin, Na$_2$SeO$_3$, ethanolamine and the growth factors indicated below. After 10 days, the plates were fixed and stained with Giemsa. Key: a) no growth factor; b) EGF alone; c) insulin alone; d) KGF alone; e) EGF and dialyzed fetal calf serum (final concentration, 10%); f) KGF and EGF; g) KGF and insulin; h) EGF and insulin. Final concentrations of the growth factors were as follows: EGF, 20 ng/ml; insulin, 10 $\mu$g/ml; and KGF, 40 ng/ml.

FIG. 7 documents the KGF cDNA nucleotide and predicted amino acid sequences. Nucleotides are numbered on the left; amino acids are numbered throughout. The N-terminal peptide sequence derived from purified KGF is underlined. The hydrophobic N-terminal domain is italicized. The potential asparagine-linked glycosylation site is overlined. The variant polyadenylation signals, AATTAA and AATACA, close to the 3' end of the RNA, are boxed.

DESCRIPTION OF SPECIFIC EMBODIMENTS

Figure 1:
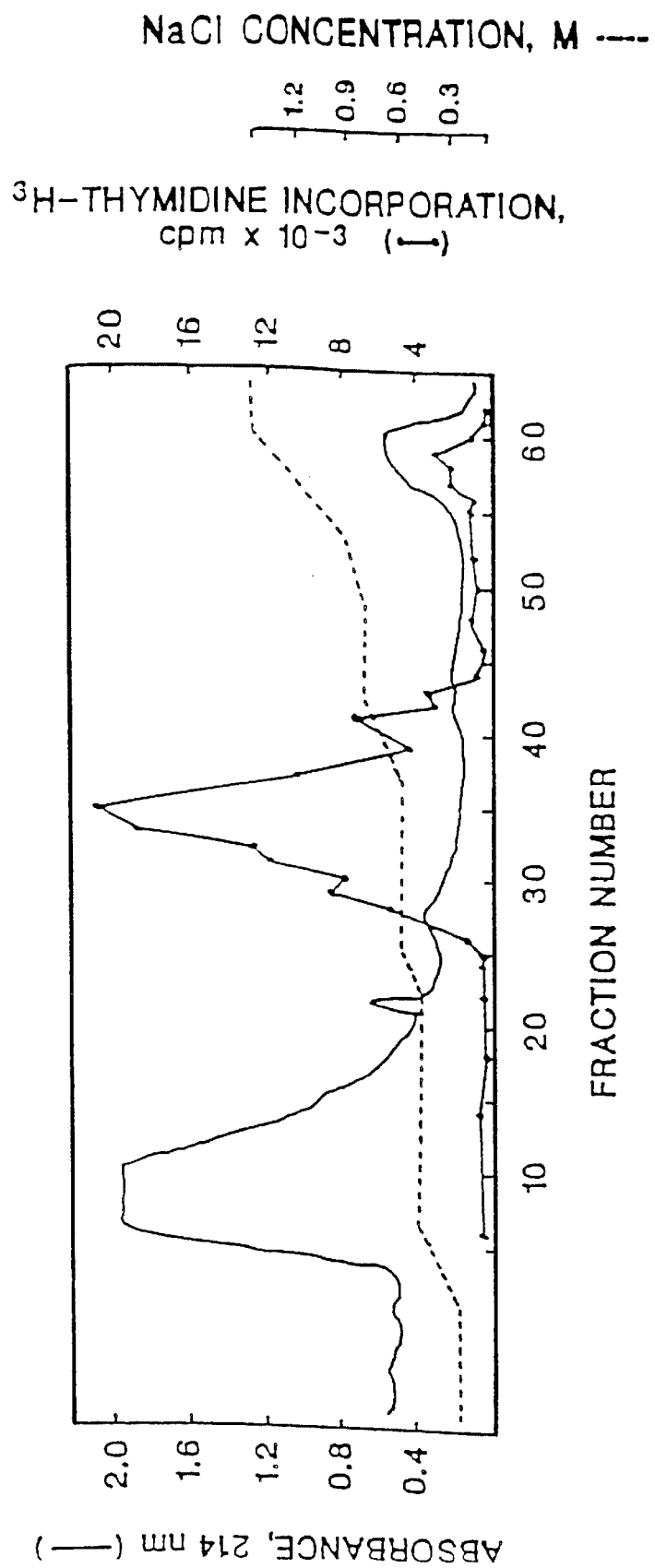
FIG. 1 depicts results of Heparin-Sepharose affinity chromatography of conditioned medium from M426 human embryonic fibroblasts. Approximately 150 ml of ultrafiltration retentate derived from five liters of M426 conditioned medium were loaded onto a heparin-Sepharose column (6 ml bed volume) in 1 hr. After washing the column with 150 ml of the equilibration buffer, 20 mM Tris-HCl, pH 7.50/0.3M NaCl, the retained protein (<5% of the total protein in the retentate) was eluted with a modified linear gradient of increasing NaCl concentration. Fraction size was 3.8 ml and flow rate during gradient elution was 108 ml/hr. Two $\mu$l of the indicated fractions were transferred to microtiter wells containing a final volume of 0.2 ml for assay of $^3$H-thymidine incorporation in BALB/MK cells as described in the Methods.

This invention relates, in part, to purified KGF or KGF-like proteins and methods for preparing these proteins. A principal embodiment of this aspect of this invention relates to homogeneous KGF characterized by an apparent molecular weight of about 28 kDa based on migration in NaDodSO$_4$/PAGE, movement as a single peak on reversed-phase high performance liquid chromatography, and a specific activity of at least about $3.4 \times 10^4$ units per milligram, and preferably at least about $3.2 \times 10^5$ units per milligram, where one unit of activity is defined as that amount which causes half of the maximal possible stimulation of DNA synthesis in certain epithelial (keratinocyte) cells under standard assay conditions outlined below.

To identify novel growth factors specific for epithelial cell types, a clonal BALB/c mouse keratinocyte cell line, designated BALB/MK (Weissman, B. E. and Aaronson, S. A. (1983) *Cell* 32, 599–606) was employed as an indicator cell to detect such factors. These cells are dependent for their growth upon an exogenous source of an epithelial cell mitogen even in medium containing serum (Weissman, B. E. and Aaronson, S. A. (1983) *Cell* 32, 599–606). The development of chemically defined medium for these cells has made it possible to demonstrate that two major mitogenic pathways are required for BALB/MK proliferation. One involves insulin-like growth factor I (or insulin at high concentration) and the other is satisfied by epidermal growth factor (EGF), transforming growth factor α (TGFα), acidic fibroblast growth factor (aFGF) or basic fibroblast growth factor (bFGF) (Falco, J. P., Taylor, W. G., DiFiore, P. P., Weissman, B. E., and Aaronson, S. A. (1988) *Oncogene* 2, 573–578).

By using BALB/MK as the prototypical epithelial cell line and NIH/3T3 as its fibroblast counterpart, conditioned media from various human cell lines were assayed for new epithelial cell-specific mitogens. These bioassays of this invention enabled the purification to homogeneity of one such novel growth factor, released by a human embryonic lung fibroblast line, and designated herein as keratinocyte growth factor (KGF).

In brief, the bioassay for KGF-like activity under standard conditions comprises the following steps:

(i) Mouse keratinocytes (BALB/MK cells) are grown in culture to confluency and then maintained for 24–72 hr in serum-free medium;

(ii) Following addition of test samples, stimulation of DNA synthesis is determined by incorporation of $^3$H-thymidine into acid-precipitable DNA.

To determine the target cell specificity of a mitogenic growth factor, the DNA synthesis stimulation, expressed as ratio of stimulated synthesis over background incorporation of thymidine in the absence of added test sample, can be compared to analogous stimulation observed in cells other than keratinocytes under the same assay conditions. In such comparisons, KGF mitogenic activity will exhibit marked specificity for the keratinocytes as opposed to fibroblasts (at least about 500-fold greater stimulation) and lesser but significant (at least about 50-fold) greater activity on keratinocytes than on other exemplary epithelial cell types (see Table 2 for further data, and Materials and Methods in Experimental Section I for details of the standard conditions of the bioassay).

By employing a method of KGF production involving culturing cells and isolating mitogenic activity, which method comprises ultrafiltration, heparin-Sepharose affinity chromatography (HSAC) and adsorptive reversed-phase high performance liquid chromatography (RP-HPLC) or, alternatively, molecular sieving HPLC (TSK-HPLC), according to the present invention, a quantity was isolated sufficient to permit detailed characterization of the physical and biological properties of this molecule.

To summarize, the method for production of KGF from producing cells such as M426 human embryonic fibroblasts (Aaronson, S. A. and Todaro, G. J. (1968) *Virology* 36, 254–261), for example, comprises the following steps:

(i) Preparation of conditioned media (e.g., 10 liters) using monolayer cultures cycled from serum-containing to serum-free medium and storing the serum-free harvest at –70° C. until further use;

(ii) Concentration by ultrafiltration using membranes having a 10 kDa molecular weight cutoff in several successive steps with intervening dilution in buffer (to facilitate removal of low molecular weight materials), followed by optional storage at –70° C.;

(iii) Affinity chromatography on heparin attached to a polymeric support (e.g., Sepharose) with elution by a gradient of increasing NaCl concentration;

(iv) Concentration by a factor of at least ten- to twenty-fold with small scale ultrafiltration devices with a 10 kDa molecular weight cutoff (e.g., a Centricon-10 microconcentrator from Amicon) and storage at –70° C.

The next step of the purification process comprises either step (v) or, alternatively, step (vi), as follows:

(v) Reversed-phase HPLC of active fractions (0.6 M NaCl pool) from the previous HSAC step in organic solvent systems;

or, (vi) Molecular sieve HPLC (e.g, on a TSK-G3000SW Glas-Pac Column from LKB) in aqueous buffer at near physiological pH (e.g., Tris-HCl, pH 6.8/0.5M NaCl) followed by storage at –70° C.

A preparation made by the TSK step (vi) was almost as pure as one obtained from RP-HPLC, as judged by silver-stained NaDodSO$_4$/PAGE (data not shown); but the TSK approach provided a far better recovery of activity (Table 1). Further, the TSK-purified material had a higher specific activity than the RP-HPLC material. KGF prepared by the TSK procedure above stimulated DNA synthesis in epithelial cells at sub-nanomolar concentrations, but failed to induce any thymidine incorporation into DNA of fibroblasts or endothelial cells at comparable or higher concentrations (up to 5 nM). The activity was sensitive to acid, heat and solvents used in the RP-HPLC step. (See Experimental Section I for data on sensitivities and further details of the production method.)

Using standard methodology well known in the art, an unambiguous amino acid sequence was determined for positions 2–13 from the amino terminus of the purified KGF, as follows: Asn-Asp-Met-Thr-Pro-Glu-Gln-Met-Ala-Thr-Asn-Val (see Experimental Section I).

The present invention also includes DNA segments encoding KGF and KGF-like polypeptides. The DNAs of this invention are exemplified by DNAs referred to herein as: human cDNA clones 32 and 49 derived from polyadenylated RNA extracted from the human embryonic lung fibroblast cell line M426; recombinants and mutants of these clones; and related DNA segments which can be detected by hybridization to these DNA segments.

As described in Experimental Section II, to search for cDNA clones corresponding to the known portion of the KGF amino acid sequence, two pools of oligonucleotide probes were generated based upon all possible nucleotide sequences encoding the nine-amino acid sequence, Asn-Asp-Met-Thr-Pro-Glu-Gln-Met-Ala. A cDNA library was constructed in a cDNA cloning vector, λpCEV9, using polyadenylated RNA extracted from the human embryonic lung fibroblast cell line M426 which was the initial source of the growth factor. Screening of the library ($9 \times 10^5$ plaques) with the $^{32}$P-labelled oligonucleotides identified 88 plaques which hybridized to both probes.

Figure 6:
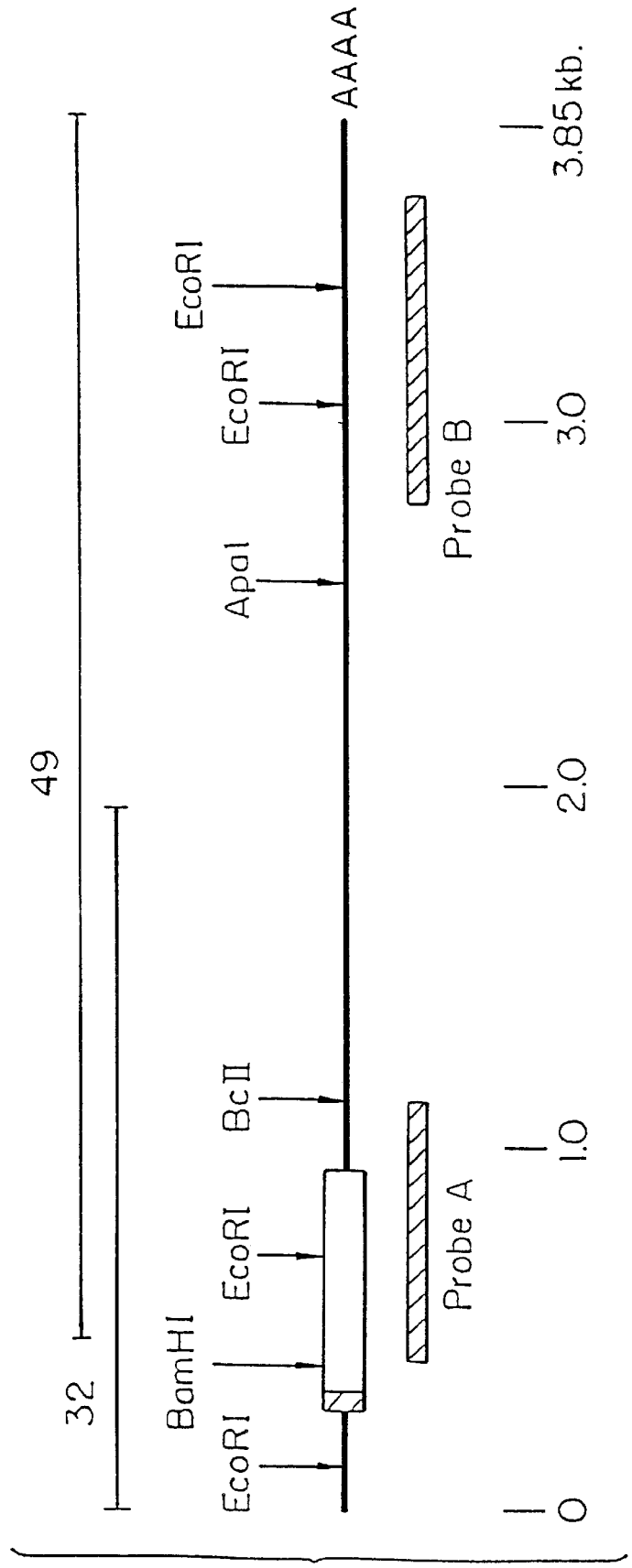
FIG. 6 outlines a schematic representation of human KGF cDNA clones. Overlapping pCEV9 clones 32 and 49, used in sequence determination, are shown above a diagram of the complete structure in which untranslated regions are depicted by a line and the coding sequence is boxed. The hatched region denotes sequences of the signal peptide. Selected restriction sites are indicated.

Of 10 plaque-purified clones that were analyzed, one, designated clone 49, had a cDNA insert of 3.5 kb, while the rest had inserts ranging from 1.8 kb to 2.1 kb. Analysis of the smaller clones revealed several common restriction sites, and sequencing of a representative smaller clone, designated clone 32, along with clone 49, demonstrated that they were overlapping cDNAs (FIG. 6). Alignment of the two cDNAs established a continuous sequence of 3.85 kb containing the complete KGF coding sequence. The sense strand DNA nucleotide sequence, and the predicted primary protein sequence encoded, are shown for the full-length composite KGF cDNA sequence in FIG. 7.

These DNAs, cDNA clones 32 and 49, as well as recombinant forms of these segments comprising the complete KGF coding sequence, are most preferred DNAs of this invention.

From the cDNA sequence, it is apparent that the primary KGF and hst translation products contain hydrophobic N-terminal regions which likely serve as signal sequences, based on similarity to such sequences in a variety of other proteins. Accordingly, this N-terminal domain is not present in the purified mature KGF molecule which is secreted by human embryonic fibroblasts.

Furthermore, KGF shares with all other members of the FGF family two major regions of homology, spanning amino acids 65–156 and 162–189 in the predicted KGF sequence, which are separated by short, nonhomologous series of amino acids of various lengths in the different family members. The sequence of the purified form of KGF contains five cysteine residues, two of which are conserved throughout the family of FGF related proteins. Five pairs of basic residues occur throughout the KGF sequence. This same pattern has been observed in other FGF family members.

It should be obvious to one skilled in the art that, by using the DNAs and RNAs of this invention in hybridization methods (such as Southern blot analyses of genomic human DNAs), especially the most preferred DNAs listed herein above, without undue experimentation, it is possible to screen genomic or cDNA libraries to find other KGF-like DNAs which fall within the scope of this invention. Furthermore, by so using DNAs of this invention, genetic markers associated with the KGF gene, such as restriction fragment length polymorphisms (RFLPs), may be identified and associated with inherited clinical conditions involving this or other nearby genes.

This invention also includes modified forms of KGF DNAs. According to a chief embodiment of this aspect of the invention, such modified DNAs encode KGF-like proteins comprising segments of amino acid sequences of KGF and at least one other member of the FGF peptide family. Thus, for example, since there is no significant N-terminal homology between the secreted form of KGF and analogous positions in other FGF-related proteins, polypeptides with novel structural and functional properties may be created by grafting DNA segments encoding the distinct N-terminal segments of another polypeptide in the FGF family onto a KGF DNA segment in place of its usual N-terminal sequence.

The polypeptide chimeras produced by such modified DNAs are useful for determining whether the KGF NH$_2$-terminal domain is sufficient to account for its unique target cell specificity. Studies on chimeras should also provide insights into which domains contribute the different effects of heparin on their biologic activities.

Indeed, the utility of this approach has already been confirmed by the successful engineering and expression of a chimeric molecule in which about 40 amino acids from the NH$_2$-terminus of the secreted form of KGF (beginning with the amino terminal cys residue of the mature KGF form, numbered 32 in FIG. 7, and ending at KGF residue 78, arg) is linked to about 140 amino acids of the C-terminal core of aFGF (beginning at residue 39, arg, and continuing to the C-terminal end of the aFGF coding sequence. This chimeric product has a target cell preference for keratinocytes, like KGF, but lacks susceptibility to heparin, a characteristic which parallels that of aFGF rather than KGF. This novel KGF-like growth factor may have advantages in clinical applications where administration of an epithelial-specific growth factor is desirable in the presence of heparin, a commonly used anticoagulant. Further details of the construction of this chimeric molecule and the properties of the polypeptide are described in Experimental Section II.

Other DNAs of this invention include the following recombinant DNA molecules comprising a KGF cDNA and any of the following exemplary vector DNAs: a bacteriophage λ cloning vector (λpCEV9); a DNA sequencing plasmid vector (a pUC variant); a bacterial expression vector (pKK233-2); or a mammalian expression vector (pMMT/neo). Such recombinant DNAs are exemplified by constructs described in detail in the Experimental Sections.

Most preferred recombinant molecules include the following: molecules comprising the coding sequence for the secreted form of KGF and a bacterial expression vector (e.g., pKK233-2) or a cDNA encoding the entire primary translation product (including the N-terminal signal peptide) and a mammalian expression vector (exemplified by pMMT) capable of expressing inserted DNAs in mammalian (e.g., NIH/3T3) cells.

Construction of recombinant DNAs containing KGF DNA and a bacterial expression vector is described in Experimental Section II. In brief, KGF cDNA was expressed to produce polypeptide in *E. coli* by placing its coding sequence under control of the hybrid trk promoter in the plasmid expression vector pKK233-2 (Amman, E. and Brosius, J. (1985) *Gene* 40, 183).

Construction of recombinant DNAs comprising KGF DNA and a mammalian vector capable of expressing inserted DNAs in cultured human or animal cells, can be carried out by standard gene expression technology using methods well known in the art for expression of such a relatively simple polypeptide. One specific embodiment of a recombinant DNA of this aspect of the present invention, involving the mammalian vector pMMT, is described further below in this section under recombinant cells of this invention.

DNAs and sense strand RNAs of this invention can be employed, in conjunction with protein production methods of this invention, to make large quantities of substantially pure KGF or KGF-like proteins. Substantially pure KGF protein thus produced can be employed, using well-known techniques, in diagnostic assays to determine the presence of receptors for this protein in various body fluids and tissue samples.

Accordingly, this invention also comprises a cell, preferably a bacterial or mammalian cell, transformed with a DNA of the invention, wherein the transforming DNA is capable of being expressed. In a preferred embodiment of this aspect of the invention, the cell transformed by the DNA of the invention produces KGF protein in a fully mitogenic form. Most preferably, these proteins will be of a secreted form (i.e., lacking an apparent signal sequence). These protein factors can be used for functional studies, and can be purified for additional biochemical and functional analyses, such as qualitative and quantitative receptor binding assays.

Recombinant *E. coli* cells have been constructed in a bacterial expression vector, pKK233-2, for production of KGF, as detailed in Experimental Section II. In summary, several recombinant bacterial clones were tested for protein production by the usual small scale methods. All recombinants tested synthesized a protein that was recognized by antibodies raised against an amino-terminal KGF peptide (see below). One recombinant was grown up in a one liter culture which produced recombinant KGF that efficiently stimulated thymidine incorporation into DNA of BALB/MK keratinocyte cells, but was only marginally active on NIH/3T3 fibroblasts. Half-maximal stimulation of the BALB/MK cells in the standard keratinocyte bioassay was achieved with a concentration of between 2 to 5 ng/ml, compared to a concentration of 10 to 15 ng/ml for KGF purified from M426 cells.

One liter of bacterial cells yielded approximately 50 $\mu$g of Mono-S purified recombinant KGF. It will be apparent to those skilled in the art of gene expression that this initial yield can be improved substantially without undue experimentation by application of a variety known recombinant DNA technologies.

Recombinant mammalian (NIH/3T3 mouse) cells have also been constructed using the entire KGF cDNA coding sequence (including the $NH_2$-terminal signal peptide) and the vector pMMT/neo, which carries mouse metallothionine (MMT) promoter and the selective marker gene for neomycin resistance. The cells are being evaluated for KGF production, particularly for secretion of the mature form (lacking signal peptide) produced by human fibroblasts, using bioassays of the present invention. This same vector and host cell combination has been used successfully to express several other similar recombinant polypeptides, including high levels of Platelet-Derived Growth Factor (PDGF) A and B chains (Sakai, R. K., Scharf, S., Faloona, F., Mullis, K. B., Norn, G. T., Erlich, H. A. and Arnheim, N. (1985) *Science* 230, 1350–1354). Accordingly, it will be recognized by those skilled in the art that high yields of recombinant KGF can be achieved in this manner, using the aforementioned recombinant DNAs and transformed cells of this invention.

Ultimately, large-scale production can be used to enable clinical testing in conditions requiring specific stimulation of epithelial cell growth. Materials and methods for preparing pharmaceutical compositions for administration of polypeptides topically (to skin or to the cornea of the eye, for example) or systemically are well known in the art and can be adapted readily for administration of KGF and KGF-like peptides without undue experimentation.

This invention also comprises novel antibodies made against a peptide encoded by a DNA segment of the invention. This embodiment of the invention is exemplified by several kinds of antibodies which recognize KGF. These have been prepared using standard methodologies well known in the art of experimental immunology, as outlined in Experimental Section II. These antibodies include: monoclonal antibodies raised in mice against intact, purified protein from human fibroblasts; polyclonal antibodies raised in rabbits against synthetic peptides with sequences based on amino acid sequences predicted from the KGF cDNA sequence [exemplified by a peptide with the sequence of KGF residues 32–45 namely, NDMTPEQMATNVR (using standard one-letter code for amino acid sequences; see FIG. 7)]; polyclonal antibodies raised in rabbits against both naturally secreted KGF from human fibroblasts and recombinant KGF produced in *E. coli* (see above).

All tested antibodies recognize the recombinant as well as the naturally occurring KGF, either in a solid-phase (ELISA) assay and/or in a Western blot. Some exemplary antibodies, which are preferred antibodies of this invention, appear to neutralize mitogenic activity of KGF in the BALB/MK bioassay.

Fragments of antibodies of this invention, such as Fab or F(ab)' fragments, which retain antigen binding activity and can be prepared by methods well known in the art, also fall within the scope of the present invention. Further, this invention comprises pharmaceutical compositions of the antibodies of this invention, or active fragments thereof, which can be prepared using materials and methods for preparing pharmaceutical compositions for administration of polypeptides that are well known in the art and can be adapted readily for administration of KGF and KGF-like peptides without undue experimentation.

These antibodies, and active fragments thereof, can be used, for example, for detection of KGF in bioassays or for purification of the protein factors. They may also be used in approaches well known in the art, for isolation of the receptor for KGF, which, as described in Experimental Section II, appears to be distinct from those of all other known growth factors.

Those preferred antibodies, and fragments and pharmaceutical compositions thereof, which neutralize mitogenic activity of KGF for epithelial cells, as indicated by the BALB/MK assay, for instance, may be used in the treatment of clinical conditions characterized by excessive epithelial cell growth, including dysplasia and neoplasia (e.g., psoriasis, or malignant or benign epithelial tumors).

This invention further comprises novel bioassay methods for detecting the expression of genes related to DNAs of the invention. In some exemplary embodiments, DNAs of this invention were used as probes to determine steady state levels of related mRNAs. Methods for these bioassays of the invention, using KGF DNAs, and standard Northern blotting techniques, are described in detail in Experimental Section II.

One skilled in the art will recognize that, without undue experimentation, such methods may be readily applied to analysis of gene expression for KGF-like proteins, either in isolated cells or various tissues. Such bioassays may be useful, for example, for identification of various classes of tumor cells or genetic defects in the epithelial growth processes.

Without further elaboration, it is believed that one of ordinary skill in the art, using the preceding description, and following the methods of the Experimental Sections below, can utilize the present invention to its fullest extent. The material disclosed in the Experimental Sections, unless otherwise indicated, is disclosed for illustrative purposes and therefore should not be construed as being limitive in any way of the appended claims.

EXPERIMENTAL SECTION I

Identification and Characterization of a Novel Growth Factor Specific for Epithelial Cells This section describes experimental work leading to identification of a growth factor specific for epithelial cells in conditioned medium of a human embryonic lung fibroblast cell line. The factor, provisionally termed keratinocyte growth factor (KGF) because of its predominant activity on this cell type, was purified to homogeneity by a combination of ultrafiltration, heparin-Sepharose affinity chromatography and hydrophobic chromatography on a $C_4$ reversed-phase HPLC column, according to methods of this invention. KGF was found to be both acid and heat labile, and consisted of a single polypeptide chain with an apparent molecular weight of approximately 28,000 daltons. Purified KGF was a potent mitogen for epithelial cells, capable of stimulating DNA synthesis in quiescent BALB/MK epidermal keratinocytes by more than 500-fold with activity detectable at 0.1 nM and maximal at 1.0 nM. Lack of mitogenic activity on either fibroblasts or endothelial cells indicated that KGF possessed a target cell specificity distinct from any previously characterized growth factor. Microsequencing revealed an amino-terminal sequence containing no significant homology to any known protein. The release of this novel growth factor by human embryonic fibroblasts indicates that KGF plays a role in mesenchymal stimulation of normal epithelial cell proliferation.

METHODS AND MATERIALS

Preparation of Conditioned Media. An early passage of M426 human embryonic fibroblasts (Aaronson, S. A. and Todaro, G. J. (1968) *Virology* 36, 254–261) was plated onto 175 $cm^2$ T-flasks and grown to confluence over 10–14 days in Dulbeccols modified Eagle's medium (DMEM; GIBCO) supplemented with 10% calf serum (GIBCO). Once confluent, the monolayers were cycled weekly from serum-containing to serum-free medium, the latter consisting of DMEM alone. The cells were washed twice with 5 ml of phosphate buffered saline prior to addition of 20 ml of DMEM. After 72 hrs, culture fluids were collected and replaced with 35 ml of serum-containing medium. The conditioned medium was stored at −70° C. until further use.

Ultrafiltration. Approximately ten liters of conditioned medium were thawed, prefiltered through a 0.50 micron filter (Millipore HAWP 142 50) and concentrated to 200 ml using the Pellicon cassette system (Millipore XX42 00K 60) and a cassette having a 10 kDa molecular weight cutoff (Millipore PTGC 000 05). After concentration, the sample was subjected to two successive rounds of dilution with one liter of 20 mM Tris-HCl, pH 7.5/0.3M NaCl, each followed by another step of ultrafiltration with the Pellicon system. Activity recovered in the retentate was either immediately applied to heparin-Sepharose resin or stored at −70° C.

Heparin-Sepharose Affinity Chromatography (HSAC). The retentate from ultrafiltration was loaded onto heparin-Sepharose resin (Pharmacia) which had been equilibrated in 20 mM Tris-HCl, pH 7.5/0.3 M NaCl. The resin was washed extensively until the optical density had returned to baseline and then subjected to a linear-step gradient of increasing Nacl concentration. After removing aliquots from the fractions for the thymidine incorporation bioassay, selected fractions were concentrated ten- to twenty-fold with a Centricon-10 microconcentrator (Amicon) and stored at −70° C.

Reversed-Phase HPLC (RP-HPLC). Active fractions (0.6 M NaCl pool) from the HSAC were thawed, pooled and further concentrated with the Centricon-10 to a final volume of $\leq 200$ μl. The sample was loaded onto a Vydac $C_4$ HPLC column (The Separations Group, Hesperia, Calif.) which had been equilibrated in 0.1% trifluoroacetic acid (TFA, Fluka)/20% acetonitrile (Baker, HPLC grade) and eluted with a linear gradient of increasing acetonitrile. Aliquots for the bioassay were immediately diluted in a 10-fold excess of 50 μg/ml BSA (Fraction V, Sigma)/20 mM Tris-HCl, pH 7.5. The remainder of the sample was dried in a Speed-Vac (Savant) in preparation for structural analysis.

Molecular Sieve HPLC. Approximately 50 μl of the twice concentrated heparin-Sepharose fractions were loaded onto a TSK-G3000SW Glas-Pac Column (LKB) which had been equilibrated in 20 mM Tris-HCl, pH 6.8/0.5M NaCl. The sample was eluted in this buffer at a flow rate of 0.4 ml/min. After removing aliquots for the bioassay, the fractions were stored at −70° C.

$NaDodSO_4$-Polyacrylamide Gel Electrophoresis ($NaDodSO_4$/PAGE). Polyacrylamide gels were prepared with $NaDodSO_4$ according to the procedure of Laemmli (Laemmli, U.K. (1970) *Nature* 227, 680–685). Samples were boiled for 3 min in the presence of 2.5% 2-mercaptoethanol (vol/vol). The gels were fixed and stained with silver (Merril, C. R., Goldman, D., Sedman, S. A. and Ebert, M. H. (1981) *Science* 211, 1437–1438) using the reagents and protocol from BioRad. Molecular weight markers were from Pharmacia.

DNA Synthesis Stimulation. Ninety-six well microliter plates (Falcon No. 3596) were precoated with human fibronectin (Collaborative Research) at 1 μg/$cm^2$ prior to seeding with BALB/MK cells. Once confluent, the cells were maintained for 24–72 hr in serum-free medium containing 5 μg/ml transferrin (Collaborative Research) and 30 nM $Na_2SeO_3$ (Baker). Incorporation of $^3$H-thymidine (5 μCi/ml final concentration, NEN) into DNA was measured during a 6 hr period beginning at 16 hrs following addition of samples. The assay was terminated by washing the cells once with ice cold phosphate-buffered saline and twice with 5% trichloroacetic acid. The precipitate was redissolved in 0.25 M NaOH, transferred into liquid scintillation fluid (Biofluor, NEN) and counted.

Stimulation of DNA synthesis was monitored as described above for BALB/MK cells on a variety of other cell lines. NIH/3T3 fibroblasts (Jainchill, J. L., Aaronson, S. A. and Todaro, G. J. (1969) *J. Virol.* 4, 549–553) were available from the National Institutes of Health, while CCL208 Rhesus monkey bronchial epithelial cells (Caputo, J. L., Hay, R. J. and Williams, C. D. ((1979) *In Vitro* 15, 222–223) were obtained from the American Type Culture Collection. The B5/589 human mammary epithelial cell line, prepared as described in (Stamfer, M. R. and Bartley, J. C. (1985) *Proc. Nail. Acad. Sci. USA* 82, 2394–2398), was obtained from Martha Stampfer (Lawrence Berkeley Laboratory, Berkeley). The mammary cells were grown in RPMI 1640 supplemented with 10% fetal calf serum and 4 ng/ml EGF. When maintained in serum-free conditions, the basal medium was DMEM. Primary cultures of human saphenous vein endothelial cells were prepared and maintained as described elsewhere (Sharefkin, J. B., Fairchild, K. D., Albus, R. A., Cruess, D. F. and Rich, N. M. (1986) *J. Surgical Res.* 41, 463–472). Epidermal growth factor and insulin were from Collaborative Research. Acidic FGF and bFGF were obtained from California Biotechnology, Inc. Recombinant TGFα was obtained from Genentech, Inc. Media and serum were either from GIBCO, Biofluids, Inc. or the NIH media unit.

Proliferation Assay. Thirty-five mm culture dishes were precoated sequentially with poly-D-lysine (20 μg/$cm^2$) (Sigma) and human fibronectin, and then seeded with approximately 2.5×$10^4$ BALB/MK cells. The basic medium was a 1:1 mixture of Eagle's low $Ca^{2+}$ minimal essential medium and Ham's F-12 medium, supplemented with 5 μg/ml transferrin, 30 nM $Na_2SeO_3$ and 0.2 mM ethanolamine (Sigma). Medium was changed every 2 or 3 days. After 10 days, the cells were fixed in formalin (Fisher Scientific Co.) and stained with Giemsa (Fisher Scientific Co.).

Protein Microsequencing. Approximately 4 μg (~150 pmol) of protein from the active fractions of the $C_4$ column were redissolved in 50% TFA and loaded onto an Applied Biosystems gas-phase protein sequenator. Twenty rounds of Edman degradation were carried out and identifications of amino acid derivatives were made with an automated on-line HPLC (Model 120A, Applied Biosystems).

RESULTS

Growth Factor Detection and Isolation. Preliminary screening of conditioned media from various cell lines indicated that media from some fibroblast lines contained mitogenic activities detectable on both BALB/MK and NIH/3T3 cells. Whereas boiling destroyed the activity on BALB/MK, mitogenic activity on NIH/3T3 remained intact. Based on the known heat stability of EGF (Cohen, S. (1962) *J. Biol. Chem.* 237, 1555–1562) and TGFα (DeLarco, J. E. and Todaro, G. J. (1978) *Proc. Natl. Acad. Sci. USA* 75, 4001–4005), it was reasoned that the BALB/MK mitogenic activity might be due to an agent different from these known epithelial growth factors.

M426, a human embryonic lung fibroblast line, was selected as the most productive source of this activity for purification of the putative growth factor(s). Ultrafiltration with the Pellicon system provided a convenient way of reducing the sample volume to a suitable level for subsequent chromatography. Various combinations of sieving, ion exchange and isoelectric focusing chromatography were tried during the development of a purification scheme, but all resulted in unacceptably low yields. On the other hand, heparin-Sepharose affinity chromatography (HSAC), which has been employed in the purification of other growth factors (Raines, E. W. and Ross, R. (1982) *J. Biol. Chem.* 257, 5154–5160; Shing, Y., Folkman, J., Sullivan, R., Butterfield, C., Murray, J. and Klagsbrun, M. (1984) *Science* 223, 1296–1299; Gospodarowicz, D., Cheng, J., Lui, G. -M., Baird, A. and Bohlen, P. (1984) *Proc. Natl. Acad. Sci. USA* 81, 6963–6967; Maciag, T., Mehlman, T., Friesel, R. and Schreiber, A. B. (1984) *Science* 225, 932–935; Conn, G. and Hatcher, V. B. (1984) *Biochem. Biophys. Res. Comm.* 124, 262–268; Lobb, R. R. and Fett, J. W. (1984) *Biochemistry* 23, 6295–6299), proved to be useful as an early purification step in the present invention. While estimates of recovered specific activity were uncertain at this stage because of the likely presence of other factors, the apparent yield-of activity was 50–70% with a corresponding enrichment of approximately 1000 fold.

As shown in FIG. 1, greater than 90% of the BALB/MK mitogenic activity eluted from the HSAC column with 0.6M NaCl. This peak of activity was not associated with any activity on NIH/3T3 cells (data not shown). A much smaller peak of BALB/MK mitogenic activity consistently emerged with 0.8–1.2M NaCl.

Due to the reproducibility of the HSAC pattern, active fractions could be identified presumptively on the basis of the gradient and optical density profile. Prompt concentration of 10–20 fold with the Centricon-10 was found to be essential for stability, which could be maintained subsequently at −70° C. for several months.

Figure 2B:
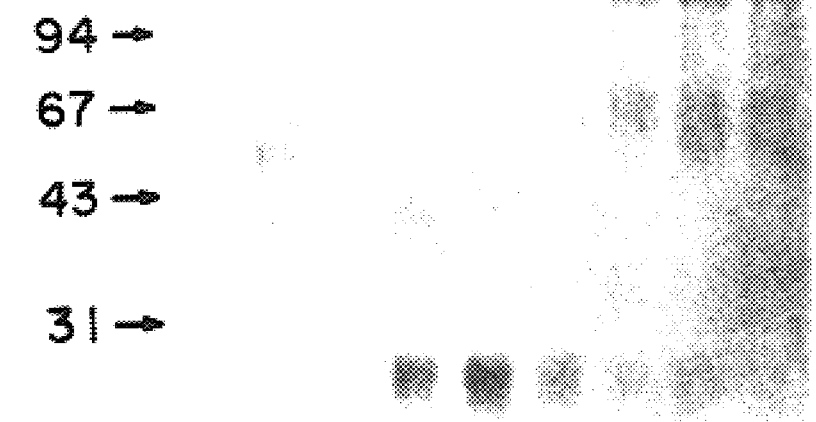

Final purification was achieved by RP-HPLC with a $C_4$ Vydac column, a preparative method suitable for amino acid sequence analysis. While the yield of activity from the $C_4$ step was usually only a few percent, this loss could be attributed to the solvents employed. In other experiments, exposure to 0.1% TFA/50% acetonitrile for 1 hr at room temperature reduced the mitogenic activity of the preparation by 98%. Nonetheless, as shown in FIG. 2A, a single peak of BALB/MK stimulatory activity was obtained, coinciding with a distinct peak in the optical density profile. The peak fractions produced a single band upon $NaDodSO_4$/PAGE and silver staining of the gel (FIG. 2B), and the relative mitogenic activity of each tested fraction (FIG. 2C) correlated well with the intensity of the bands across the activity profile.

Figure 3:
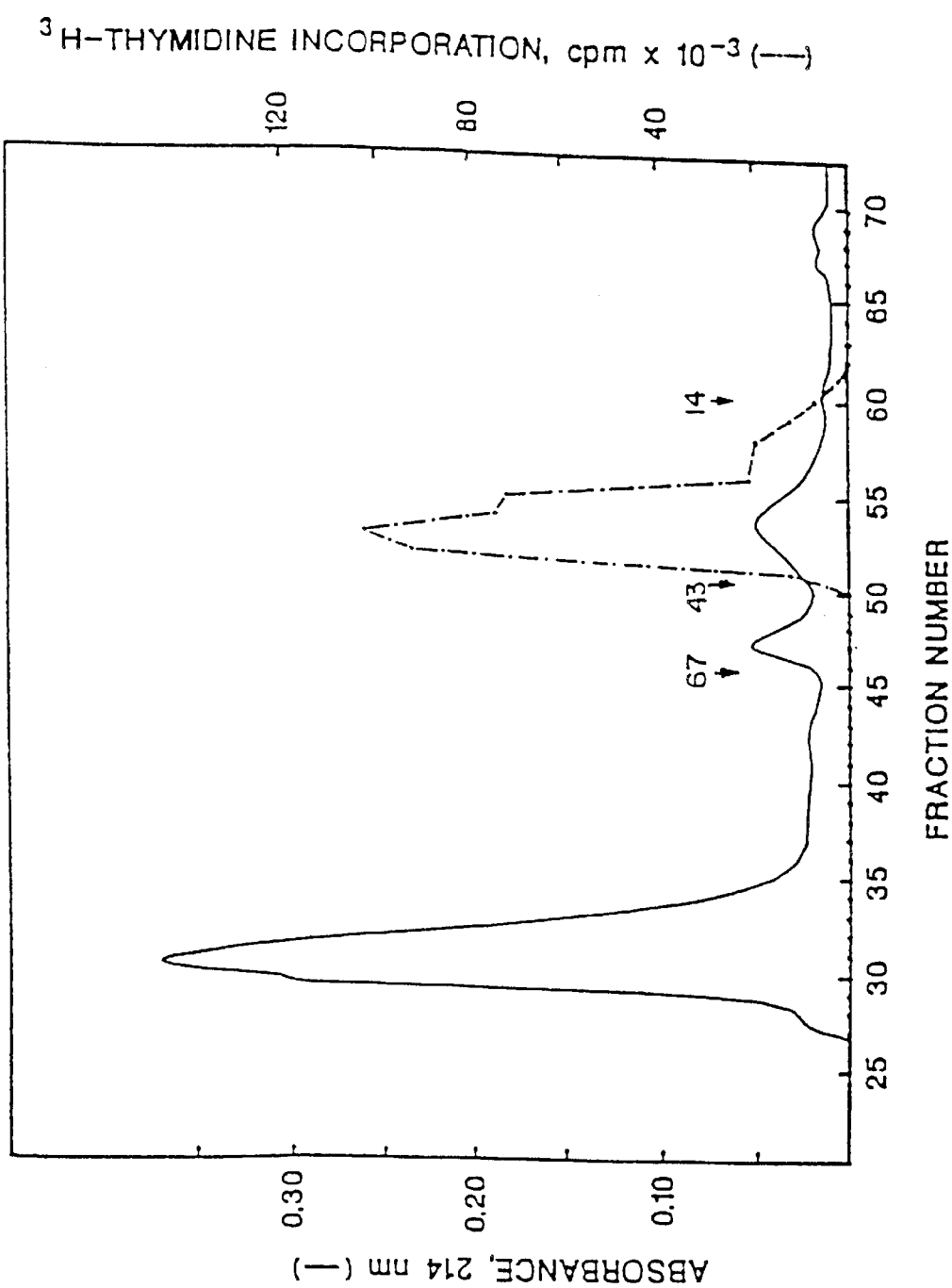
FIG. 3 presents an alternative purification step to RP-HPLC, using molecular sieving HPLC (TSK 3000SW) chromatography of the BALB/MK mitogenic activity. Approximately 50 $\mu$l of a Centricon-processed, 0.6M NaCl pool from HSAC were loaded onto a LKB GlasPac TSK G3000SW column (8×300 mm), previously equilibrated in 20 mM Tris-HCl, pH 6.8/0.5M NaCl, and eluted as 0.2 ml fractions at a flow rate of 0.4 ml/min. Aliquots of 2 $\mu$l were transferred to microtiter wells containing a final volume of 0.2 ml for assay of $^3$H-thymidine incorporation in BALB/MK cells. The elution positions of molecular weight markers (mass in kDa) were as indicated by the arrows.

An alternative purification step to the HPLC technique described above, using sieving chromatography with a TSK G3000SW GlasPac column run in aqueous solution near physiological pH, resulted in a major peak of activity in the BALB/MK bioassay (FIG. 3). This preparation was almost as pure as the one obtained from RP-HPLC as judged by silver-stained $NaDodSO_4$/PAGE (data not shown) but provided a far better recovery of activity (Table 1). The TSK-purified material was used routinely for biological studies as it had a higher specific activity.

In both types of purified preparations (i.e., purified by HPLC or molecular sieving), the profile of mitogenic activity was associated with a distinct band on $NaDodSo_4$/PAGE which appeared to be indistinguishable in the two preparations.

TABLE 1

Growth Factor Purification

| Purification step | Protein (mg) | Total activity (units)* | Specific activity (units/mg) |
|---|---|---|---|
| Conditioned medium (10 liters) | $1.4 \times 10^{3a}$ | $2.5 \times 10^4$ | $1.8 \times 10^1$ |
| Ultrafiltration (retentate) | $1.3 \times 10^{3a}$ | $3.2 \times 10^4$ | $2.5 \times 10^1$ |
| HSAC 0.6 MM NaCl pool | $0.73^b$ | $1.6 \times 10^4$ | $2.2 \times 10^4$ |
| TSK-G3000 SW | $8.4 \times 10^{-3b}$ | $2.7 \times 10^3$ | $3.2 \times 10^5$ |
| $C_4$-HPLC | $6.1 \times 10^{-3b}$ | $2.1 \times 10^2$ | $3.4 \times 10^4$ |

*One unit of activity is defined as half of the maximal stimulation of thymidine incorporation induced by TSK-purified factor in the BALB/MK bioassay, in which approximately 3 ng of the TSK-purified factor stimulated 1 unit of activity.

Recoveries were calculated by assuming that all of the mitogenic activity in the starting material was due to the isolated factor.

Physical and Biological Characterization of the Growth Factor. The purified factor had an estimated molecular weight of about 28 kDa based on $NaDodSO_4$/PAGE under reducing (FIGS. 2A–2C) and non-reducing conditions (data not shown). This value was in good agreement with its elution position on two different sizing columns run in solvents expected to maintain native conformation (TSK-G3000-SW, FIG. 3, and superose-12, data not shown). From these data, the mitogen appears to consist of a single polypeptide chain with a molecular weight of 25–30 kDa.

The heat and acid lability of the mitogenic activity were demonstrated using the BALB/MK mitogenesis bioassay. While activity was unaffected by a 10 min incubation at 50° C., it was reduced by 68% after 10 min at 60° C. and was undetectable after 3 min at 100° C. Exposure to 0.5M acetic acid for 60 min at room temperature resulted in a decline in activity to 14% of the control. In comparison, the mitogenic activity of the known growth factor, EGF, was not diminished by any of these treatments.

Figure 4:
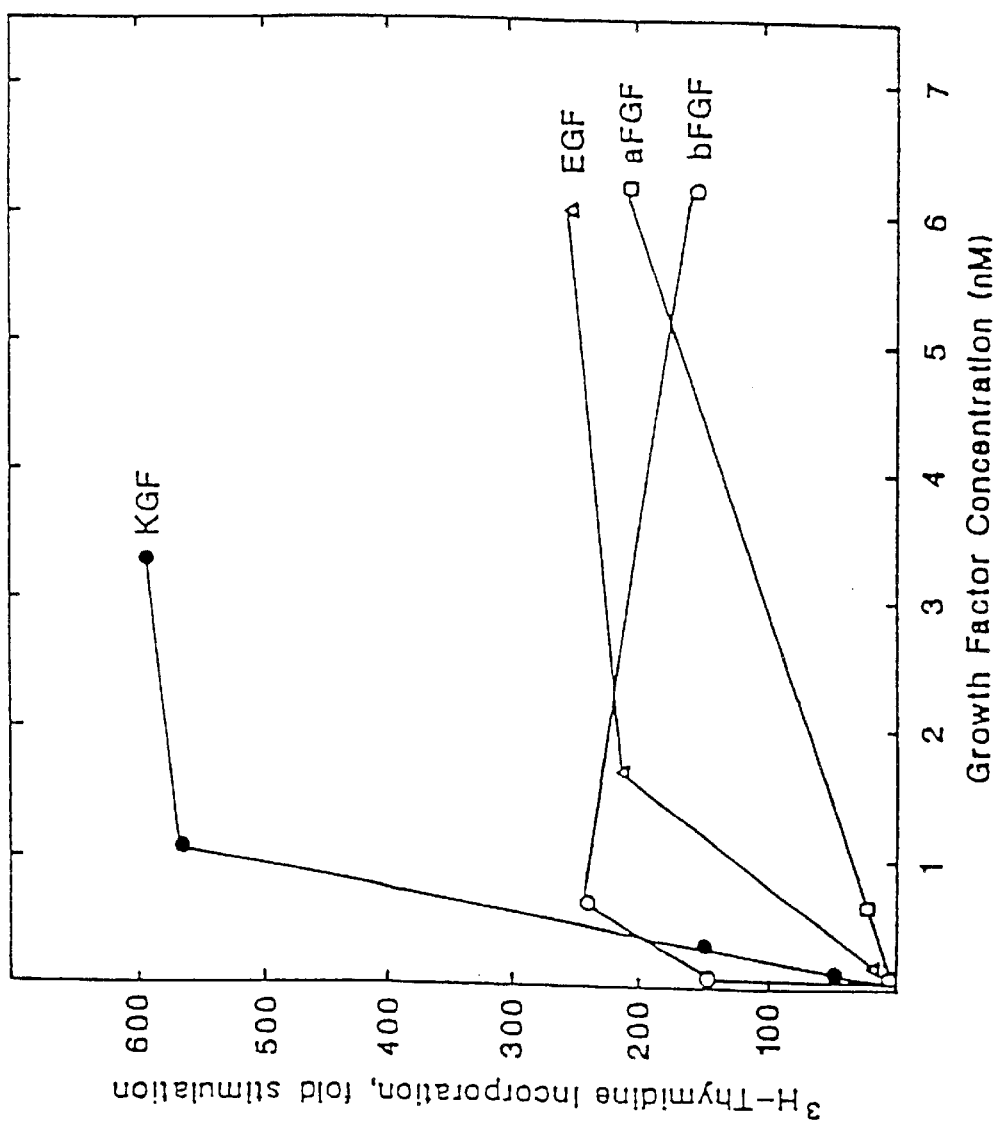
FIG. 4 illustrates a comparison of BALB/MK DNA synthesis in response to TSK-purified mitogen and other growth factors. Incorporation of $^3$H-thymidine into trichloracetic acid-insoluble DNA, expressed as fold stimulation over background, was measured as a function of the concentration of the indicated growth factors. Background values with no sample added were 150 cpm. The results represent mean values of two independent experiments. Replicates in each experiment were within 10% of mean values. TSK-purified mitogen, •__•; EGF, ∆__∆; aFGF, ▯__▯; bFGF, ○__○.

The dose response curve for the purified growth factor depicted in FIG. 4 illustrates that as little as 0.1 nM led to a detectable stimulation of DNA synthesis. Thus, the activity range was comparable to that of the other growth factors analyzed to date. A linear relationship was observed in the concentration range 0.1–1.0 nM with maximal stimulation of 600 fold observed at 1.0 nM. The novel factor consistently induced a higher level of maximal thymidine incorporation than EGF, aFGF, or bFGF in the BALB/MK keratinocytes (FIG. 4).

The distinctive target cell specificity of this factor was demonstrated by comparing its activities on a variety of cell types with those of other growth factors known to possess epithelial cell mitogenic activity. As shown in Table 2, the newly isolated factor exhibited a strong mitogenic effect on BALB/MK but also induced demonstrable incorporation of thymidine into DNA of the other epithelial cells tested. In striking contrast, the factor had no detectable mitogenic effects on mouse (or human, data not shown) fibroblasts or human saphenous vein endothelial cells.

By comparison, none of the other known growth factors appeared to preferentially stimulate keratinocytes. TGFα and EGF showed potent activity on fibroblasts, while the FGFs were mitogenic for endothelial cells as well as fibroblasts (Table 2). Because of its specificity of epithelial cells and the sensitivity of keratinocytes in particular, the novel mitogen was provisionally designated as keratinocyte growth factor (KGF).

To establish that KGF not only would stimulate DNA synthesis but would also support sustained cell growth, the ability of BALB/MK cells to grow in a fully-defined, serum-free medium supplemented with this growth factor was assessed. As shown in FIG. 5, the KGF served as an excellent substitute for EGF but not insulin (or insulin-like growth factor I) in this chemically defined medium. Thus, KGF appears to act through the major signalling pathway shared by EGF, aFGF and bFGF for proliferation of BALB/MK cells.

TABLE 2

Target Cell Specificity of Growth Factors

| Growth Factor | Epithelial | | | Fibroblast | Endothelial |
| --- | --- | --- | --- | --- | --- |
| | BALK/MK | BS/589 | CCL208 | NIH/3T3 | Human saphenous vein |
| KGF | 500–1000 | 2–3 | 5–10 | <1 | <1 |
| EGF | 100–200 | 20–40 | 10–30 | 10–20 | n.d. |
| TGFa | 150–300 | n.d. | n.d. | 10–20 | n.d. |
| aFGF* | 300–500 | 2–3 | 5–10 | 50–70 | 5 |
| bFGF | 100–200 | 2–3 | 2–5 | 50–70 | 5 |

*Maximal stimulation by aFGF required the presence of heparin (Sigma), 20 μg/ml.
n.d. = not determined.

Microsequencing Reveals a Unique N-terminal Amino Acid Sequence of KGF. To further characterize the growth factor, approximately 150 pmol of $C_4$-purified material were subjected to amino acid sequence analysis. A single sequence was detected with unambiguous assignments made for cycles 2–13, as follows: X-Asn-Asp-Met-Thr-Pro-Glu-Gln-Met-Ala-Thr-Asn-Val. High background noise precluded an assignment for the first position which is, therefore, indicated by an X.

A computer search using the FASTP program (Lipman, D. J. and Pearson, R. W. (1985) Science 227, 1435–1441) revealed that the N-terminal amino acid sequence of KGF showed no significant homology to any protein in the National Biomedical Research Foundation data bank, thus supporting the novelty of this epithelial growth factor.

DISCUSSION

The studies described in this Experimental Section identified a human growth factor which has a unique specificity for epithelial cells. By employing ultrafiltration, HSAC and RP-HPLC or TSK sieving chromatography according to the present invention, a quantity sufficient to permit detailed characterization of the physical and biological properties of this molecule was isolated.

A single silver-stained band corresponding to a molecular weight of about 28,000 daltons was detected in the active fractions from RP-HPLCD, and the intensity of the band was proportional to the level of mitogenic activity in these fractions. A band indistinguishable from that obtained by RP-HPLC was seen in the active fractions from TSK chromatography. The purified protein stimulated DNA synthesis in epithelial cells at sub-nanomolar concentrations, but failed to induce any thymidine incorporation in fibroblasts or endothelial cells at comparable or higher concentrations (up to 5 nM). This distinctive target cell specificity combined with the single novel N-terminal amino acid sequence determined from the purified molecule lead to the conclusion that KGF represents a new growth factor.

In a chemically defined medium the purified factor was able to complement the insulin-like growth factor I/insulin growth requirement of BALB/MK cells and therefore must act through a signal transduction pathway shared with EGF, TGFα and the FGFs. Moreover, the new factor was more potent than any of the known epithelial cell mitogens in stimulating thymidine incorporation in BALB/MK cells. Preliminary evidence indicates that this factor is also capable of supporting proliferation of secondary cultures of human keratinocytes (data not shown).

Handling and storage of KGF was problematical during its purification. Besides its inherent lability to acid and heat, it was unstable to lyophilization or dialysis. After HSAC, complete loss of activity occurred within 24 hr despite the use of carrier proteins, heparin, protease inhibitors, siliconized tubes or storage at either 4° or −20° C. Only concentrating the sample at this stage could preserve its activity.

Furthermore, in order to transfer the dried, purified factor it was necessary to utilize either strong acid or detergent, consistent with an adsorptive tendency or insolubility. Thus, for preservation of activity, the purified factor was maintained in solution at high concentrations at −70° C. where it remained stable for several months.

The ability of KGF to bind heparin may signify a fundamental property of this factor that has a bearing on its function in vivo. Growth factors with heparin-binding properties include aFGF (Maciag, T., Mehlman, T., Mehlman, T., Friesel, R. and Schreiber, A. B. (1984) Science 225, 932–935; Conn, G. and Hatcher, V. B. (1984) Biochem. Biophys. Res. Comm. 124, 262–268; Lobb, R. R. and Fett, J. W. (1984) Biochemistry 23, 6295–6299), bFGF (Gospodarowicz, D., Cheng, J., Lui, G. -M., Baird, A. and Bohlen, P. (1984) Proc. Natl. Acad. Sci. USA 81, 6963–6967, Lobb, R. R. and Fett, J. W. (1984) Biochemistry 23, 6295–6299) granulocyte/macrophage colony stimulating factor (Roberts, R., Gallagher, J., Spooncer, E., Allen, T. D., Bloomfield, F. and Dexter, T. M. (1988) Nature 332, 376–378) and interleukin 3 (Roberts, R., Gallagher, J., Spooncer, E., Allen, T. D., Bloomfield, F. and Dexter, T. M. (1988) Nature 332, 376–378). Each of these is produced by stromal cells (Roberts, R., Gallagher, J., Spooncer, E., Allen, T. D., Bloomfield, F. and Dexter, T. M. (1988) Nature 332, 376–378; Libermann, T. A., Friesel, R., Jaye, M., Lyall. R. M., Westermark, B., Drohen, W., Schmidt, A., Maciag, T. and Schlessinger, J. (1987) EMBOJ., 61 1627–1632; Shipley, G. D., Sternfeld, M. D., Coffey, R. J. and Pittelkow, M. R. (1988) *J. Cell Biochem. Supp* 12A, 125, abstr. C420). Such factors appear to be deposited in the extracellular matrix, or on proteoglycans coating the stromal cell surface (Roberts, R., Gallagher, J., Spooncer, E., Allen, T. D., Bloomfield, F. and Dexter, T. M. (1988) *Nature* 332, 376–378, Vladavsky, I., Folkman, J., Sullivan, R., Fridman, R., Ishai-Michaeli, R., Sasse, J. and Klagsburn, M. (1987) *Proc. Natl. Acad. Sci. USA* 84, 2292–2296). It has been postulated that their storage, release and contact with specific target cells are regulated by this interaction (Roberts, R., Gallagher, J., Spooncer, E., Allen, T. D., Bloomfield, F. and Dexter, T. M. (1988) *Nature* 332, 376–378, Vlodavsky, I., Folkman, J., Sullivan, R., Fridman, R., Ishai-Michaeli, R., Sasse, J. and Klagsburn, M. (1987) *Proc. Natl. Acad. Sci. USA* 84, 2292–2296). While mesenchymal-derived effectors of epithelial cell proliferation have also been described (Gilchrest, B. A., Karassik, R. L., Wilkins, L. M., Vrabel, M. A. and Maciag, T. (1983) *J. Cell Physiol.* 117, 2325–240, Chan, K. Y. and Haschke, R. H. (1983) *Exp. Eye Res.* 36, 231–246, Stiles, A. D., Smith, B. T. and Post, M. (1986) *Exp. Lung Res.* 11, 165–177), their identities have not been elucidated. Its heparin-binding properties, release by human embryonic fibroblast stromal cells, and epithelial cell tropism provide KGF with all of the properties expected of such a paracrine mediator of normal epithelial cell growth.

The partial amino acid sequence determined for this new growth factor has enabled molecular cloning of its coding sequence and determination of its structural relationship to known families of growth factors, as described in Experimental Section II, below.

EXPERIMENTAL SECTION II cDNA Sequence of a Novel Epithelial Cell Specific Growth Factor Defines a New Member of the FGF Family Work in the previous Experimental Section I identified and purified a novel heparin-binding growth factor, designated keratinocyte growth factor (KGF), which is particularly active on keratinocytes and appears to be specific for epthelial cells. This second Experimental Section describes the isolation and characterization of cDNA clones encoding KGF, using synthetic oligonucleotides, based upon the experimentally determined N-terminal amino acid sequence, as hybridization probes. Nucleotide sequence analysis identified a 582-bp open reading frame which would code for a 194-amino acid polypeptide that is between 41% and 33% identical to the heparin-binding acidic and basic fibroblast growth factors (FGFs), and the related products of the hst and int-2 oncogenes. The KGF gene RNA transcript is expressed in normal fibroblasts of both embryonic and adult origin, but not is epithelial, endothelial or glial cells. Thus, KG appears to be normally expressed by the mesenchyme, indicating a role in the regulation of epithelial cell proliferation.

MATERIALS AND METHODS

Isolation of cDNA clones. The purification and N-terminal sequencing of KGF has been previously described (see Experimental Section I, above and Rubin, J. S., Osada, H., Finch, P. W., Taylor, W. G., Rudikoff, S. and Aaronson, S. A. (1989) *Proc. Natl. Acad. Sci. USA* (in press), February, 1988). Pools (50 pmole) of deoxyoligonucleotides described under Results were 5' end-labelled using 83 pmole of τ-$^{32}$P-ATP (3000 Ci/mmole, Amersham) and 10 units of T4 polynucleotide kinase. The recombinant phage carrying cDNA clones were replica plated onto nitrocellulose filters and hybridized with $^{32}$P-labelled deoxyoligonucleotides in 20% fomamide, 10% dextran sulphate, 10 mM Tris-HCl (pH 7.5), 8× SSC, 5× Denhardt's and 50 μg/ml denatured salmon sperm DNA, overnight at 42° C. Filters were washed in 0.5× SSC, 0.1% SDS at 50° C. and exposed to Kodak X-omat AR film.

DNA sequencing. The nucleotide sequence of the KGF cDNA was determined by the dideoxy chain termination method (Sanger, F., Nicklen, S. and Coulson, A. R. (1977) *Proc. Natl. Acad. Sci. USA* 74, 5463–5467), of overlapping restriction fragments, subcloned into pUC vectors (Yanisch-Perron, C., Vieira, J. and Messing, J. (1985) *Gene* 33, 103–119)

Construction of a bacterial expression vector for KGF cDNA. KGF cDNA encoding the mature, secreted form of the polypeptide was placed under control of the hybrid trk promoter in the plasmid expression vector pKK233-2 (Amman, E. and Brosius, J. (1985) *Gene* 40, 183), as follows. To accomplish this, a specific length of KGF cDNA that contained the information to code for the mature KGF molecule (i.e., without its signal peptide) was amplified using the polymerase chain reaction (PCR) technique (Sakai, R. K., Scharf, S., Faloona, F., Mullis, K. B., Norn, G. T., Erlich, H. A. and Arnheim, N. (1985) *Science* 230, 1350–1354). The fragment was directionally inserted between two sites in the vector, namely the NcoI site, made blunt ended by S1 nuclease digestion, and the HindIII site, using standard recombinant DNA methodology. The ends of the KGF cDNA produced by the PCR method were as follows: the 5' end was blunt and began with an ATG codon, followed by the codon TGC for cys residue, number 33, which is the amino terminal residue of the mature form of KGF (see FIG. 7), and then the entire KGF coding sequence. The stop codon, TAA, and the four bases immediately following, TTGC, were also included on the 3' end of the cDNA. The primer used in the PCR method to direct DNA synthesis to the desired position on the 3' end of the cDNA included a HindIII site for insertion of the amplified cDNA into the vector DNA.

Production of antibodies against KGF and KGF-related peptides. Monoclonal antibodies were raised in mice against intact, purified protein from human fibroblasts using 5 or more subcutaneous injections. Test bleeds were screened with a solid-phase (ELISA) assay using highly purified KGF from human epithelial cells as antigen. Hybridomas were prepared by routine methods and supernatants were screened with the ELISA assay to detect KGF-reactive antibodies. Positive clones were serially subcloned by the usual methods, and selected subclones were grown as ascites tumors in mice for production of large amounts of antibodies. Antibodies were purified from ascites fluids employing standard techniques (e.g., hydroxyapatite or immunoaffinity resins).

Polyclonal antibodies against a synthetic peptide were raised in rabbits by standard methods, as follows. The peptides were made by solid phase technology and coupled to thyroglobulin by reaction with glutaraldehyde. Serial subcutaneous injections were made and test bleeds were screened by ELISA as well as other techniques, including Western blot analysis and mitogenesis bioassay. IgG immunoglobulins were isolated by affinity chromatography using immobilized protein G.

Polyclonal antibodies were raised in rabbits against both naturally secreted by KGF from human fibroblasts and recombinant KGF produced in *E. coli* (see next section), using the following protocol:

i) Initial injection and first boost were administered in the inguinal lymph nodes;

ii) subsequent boost were made intramuscularly. Screening of test bleeds included ELISA as well as Western blot analysis and mitogenesis bioassay, and IgG was purified as for antibodies against synthetic peptides, above.

RESULTS

Isolation of cDNA clones encoding the novel growth factor. To search for cDNA clones corresponding to the KGF coding sequence, two pools of oligonucleotides with lengths of 26 bases were generated based upon a nine-amino acid sequence, Asn-Asp-Met-Thr-Pro-Glu-Gln-Met-Ala, as determined by microsequencing of purified KGF (see Experimental Section I, above and reference Rubin et al., *Proc. Natl. Acad. Sci. USA* 86:802–806 (1989). One oligonucleotide pool contained a mixture of all 256 possible coding sequences for the nine amino acids, while the other contained inosine residues at the degenerate third position of the codons for Thr and Pro.

This latter design reduced the number of possible coding sequences in the pool to 16. Inosine in a tRNA anticodon can form hydrogen bonds with A, C or U (Crick, F. H. C. (1966) *J. Mol. Biol.* 19, 548–555), and oligonucleotides that contain deoxyinosine have been shown to hybridize efficiently with the corresponding cDNA (Ohtsuka, E., Matsuki, S., Ikehara, M., Takashi, Y. and Matsubara, K. (1985) *J. Biol. Chem.* 260, 2605–2608).

A cDNA library was constructed in a cDNA cloning vector, pCEV9 (Miki, T., Matsui, t., Heidara, M. and Aaronson, S. A., unpublished observations) using polyadenylated RNA extracted from the human embryonic lung fibroblast cell line M426 (Aaronson, S. A. and Todaro, G. J. 1968, *Virology* 36, 254–261), the initial source of the growth factor. Screening of the library (9×10$^5$ plaques) with the $^{32}$P-labelled 26-mer oligonucleotides identified 88 plaques which hybridized to both pools of oligonucleotide probes.

Characterization and sequencing of selected cDNA clones. Of 10 plaque-purified clones that were analyzed, one, designated clone 49, had a cDNA insert of 3.5 kb, while the rest had inserts ranging from 1.8 kb to 2.1 kb. Analysis of the smaller clones revealed several common restriction sites. Sequencing of a representative smaller clone, designated clone 32, along with clone 49, demonstrated that they were overlapping cDNAs (FIG. 6).

Description of the sequence encoding the KGF polypeptide. Alignment of the two cDNAs (clones 32 and 49) established a continuous sequence of 3.85 kb containing the complete KGF coding sequence (FIG. 7). An ATG likely to be an initiation codon was located at nucleotide position 446 establishing a 582-base pair open reading frame that ended at a TAA termination codon at position 1030. This open reading frame would encode a 194-amino acid polypeptide with a calculated molecular weight of 22,512 daltons.

The sequence flanking the ATG codon did not conform to the proposed GCC(G/A)CCATGG consensus for optimal initiation by eukaryotic ribosomes (Kozak, M. (1987) *Nucl. Acids Res.* 13, 8125–8148), however, there was an A three nucleotides upstream of the ATG codon. An A at this position is the most highly conserved nucleotide in the consensus. This ATG codon was preceded 85 nucleotides upstream by a TGA stop codon in the same reading frame.

A 19-amino acid sequence that was homologous to the experimentally determined N-terminus of purified KGF began 32 amino acids downstream of the proposed initiation codon. There was complete agreement between the predicted and experimentally determined amino acid sequences, where unambiguous assignments could be made.

To search for homology between KGF and any known protein, a computer search of the National Biomedical Research Foundation data base using the FASTP program of Lipman and Pearson was conducted (Lipman, D. J. and Pearson, R. W. (1985) *Science* 227, 1435–1443). By this approach, a striking degree of relatedness between the predicted primary structure of KGF and these of acidic and basic FGF, as well as the related hst, FGF-5 and int-2-encoded proteins was revealed.

Figure 8:
FIG. 8 shows identification of KGF mRNAs by Northern blot analysis. Lanes a and c, poly(A)-selected M426 RNA; lanes b and d, total cellular M426 RNA. Filters were hybridized with a $^{32}$P-labeled 695 bp BamHI/BclI fragment from clone 32 (Probe A, FIG. 6), lanes a and b, or a 541 bp ApaI/EcoRI fragment from clone 49 (Probe B, FIG. 6), lanes c and d.

Expression of mRNA transcripts of the KGF gene in human cells. In preliminary attempts to examine expression of KGF mRNA in human cells, a probe spanning the majority of the KGF coding sequence (Probe A, FIG. 6) detected a single 2.4 kb transcript by Northern blot analysis of total M426 RNA (FIG. 8). This was considerably shorter than the length of the composite cDNA sequence, 3.85 kb.

However, on screening poly(A)-selected M426 RNA, an additional transcript of approximately 5 kb was detected. Furthermore, a probe derived from the untranslated region of clone 49, 3' to the end of clone 32 (Probe B, FIG. 6), hybridized only to the larger message (FIG. 8). Thus, it appears that the KGF gene is transcribed as to alternate RNAs. Two other members of the FGF gene family, bFGF (Abraham J. A., et al., (1986) *Science* 233, 545–548) and int-2 (Mansour, S. L. and Martin, G. R. (1988) *EMBO J.* 1, 2035–2041), also express multiple RNAs, the significance of which remains to be determined.

Figure 10:
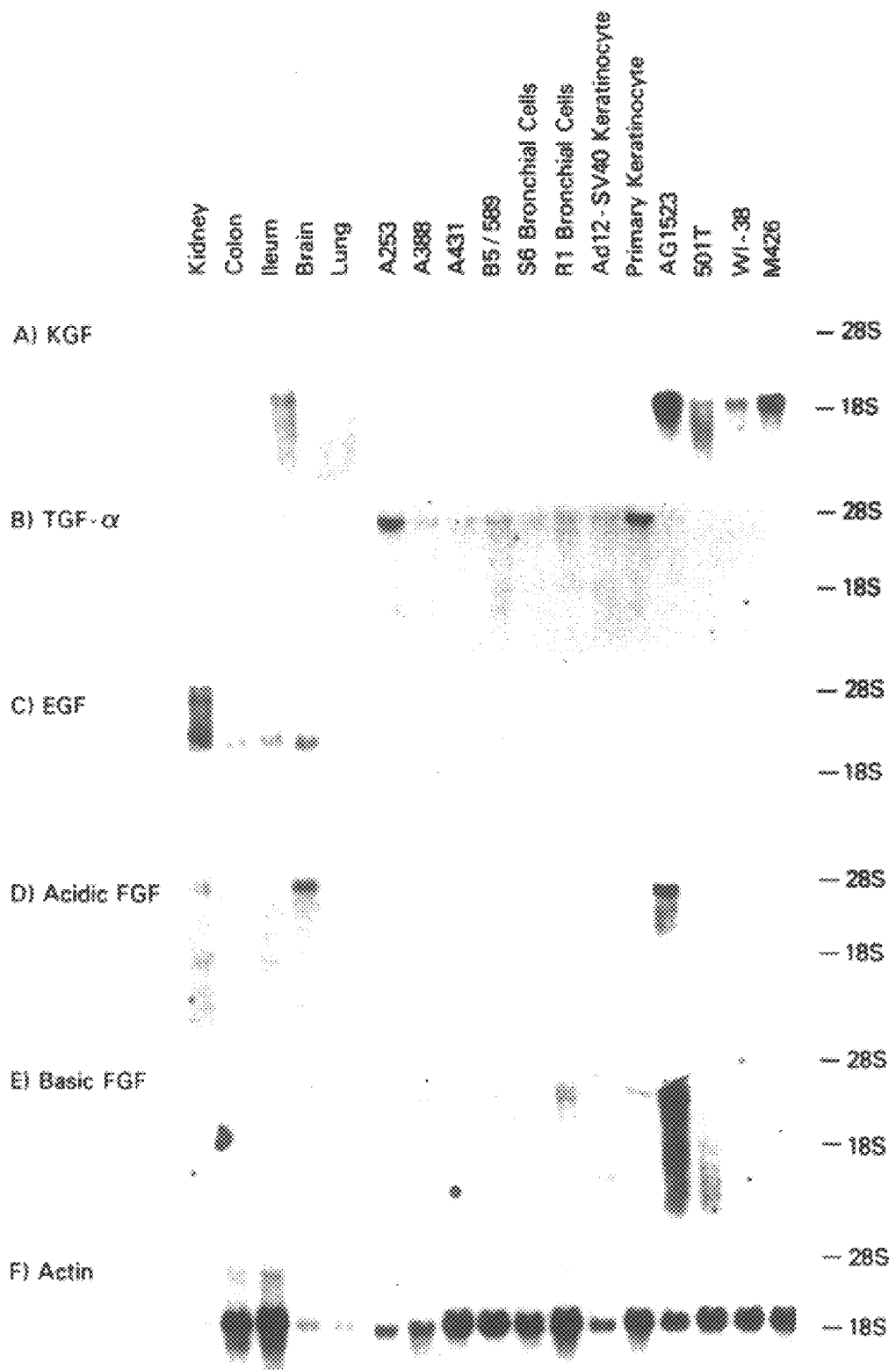
FIG. 10 shows northern blot analysis of KGF mRNA in normal human cell lines and tissues, and comparison with mRNA expression of other growth factors with known activity on epithelial cells. Total cellular RNAs were isolated by cesium trifluoro-acetate gradient centrifugation. 10 $\mu$g of RNA were denatured and electrophoresed in 1% formaldehyde gels. Following milk alkali denaturation (50 mM NaOH for 30'), RNA was transferred to nitrocellulose filters using 1 M ammonium acetate as a convectant. Filters were hybridized to a $^{32}$P-labelled cDNA probe containing the 647 bp EcoR1 fragment from the 5' end of the KGF coding sequence (A) or similar probes from the other growth factor DNAs. The following human cell types were used: squamous cell carcinomas (A253, A388 and A431); mammary epithelial cells (B5/589); immortalized bronchial epithelial cells (S6 and R1); keratinocytes immortalized with Ad12-SV40; primary human keratinocytes; neonatal foreskin fibroblasts, (AG1523); adult skin fibroblasts (501T); and embryonic lung fibroblasts (WI-38 and M426), and tissues, revealing that a single 2.4 kb transcript was present in RNA from human embryonic lung fibroblasts and from adult skin fibroblasts, while no transcript was detected in the (B5/589) epithelial or (HA 83) glial cell lines or in primary cultures of human saphenous vein endothelial cells.

To investigate the normal functional role of KGF, the expression of its transcript in a variety of human cell lines and tissues was examined. As shown in FIG. 10, the predominant 2.4 kb KGF transcript was detected in each of several stromal fibroblast lines derived from epithelial tissues of embryonic, neonatal and adult sources, but not from epithelial cell lines of normal origin. The transcript was also detected in RNA extracted from normal adult kidneys and organs of the gastrointestinal tract, but not from lung or brain. The striking specificity of KGF RNA expression in stromal cells from epithelial tissues indicated that this factor plays a normal role in mesenchymal stimulation of epithelial cell growth.

For comparison, the mRNAs of other growth factors with known activity on epithelial cells were also analyzed in the same tissues as listed above. Among the epithelial and stromal cell lines analyzed, there was no consistent pattern of expression of aFGF or bFGF transcripts (FIG. 10). The EGF transcript was not expressed in any of the same cell lines, and was only observed in kidney, among the various tissues. Finally, the TGFα message was not detected in any of the stromal fibroblast lines and was expressed at varying levels in each of the epithelial cell lines. It was also detected at low levels in kidney among the tissues examined (FIG. 10).

Inhibition of KGF mitogenic activity by heparin. Heparin has been shown to substantially increase the mitogenic activity of aFGF for a variety of target cells in culture, and to stabilize it from heat inactivation (Schreiber, et al., *Proc. Natl. Acad. Sci USA* 82:6138–6142 (1985), Gospodarowicz et al., *J. Cell Physiol.* 128:475–485 (1986)). Despite binding tightly to bFGF, heparin had minimal effects on its mitogenic activity (Gospodarowicz et al., supra). In view of the relatedness of KGF to the FGFs, the effect of heparin on KGF mitogenic activity was examined. As shown in Table 3, thymidine incorporation by BALB/MK cells in response to KGF was inhibited 16 fold when heparin was included in the culture medium. In contrast, the activities of both aFGF and bFGF were increased by the same treatment.

TABLE 3

Effect of Heparin on KGF Mitogen Activity.

| Growth Factor | BALB/MK | | NIH/3T3 | |
|---|---|---|---|---|
| | − | + | − | + |
| KGF | 150 | 9.5 | <1 | <1 |
| aFGF | 106 | 259 | 10.4 | 68 |
| bFGF | 30 | 124 | 45.7 | 70 |

Cells were plated in microtiter plates, grown to confluence in serum containing media and then placed in a serum-free medium for 24–72 hr prior to sample addition. Mitogenesis assays were performed as described (see Experimental Section I, above Rubin et al., *Proc. Natl. Acad. Sci. USA* 86:802–806 (1989). Where indicated, heparin was included in the culture media at a final concentration of 20 μg/ml. The concentration of all the growth factors was 50 ng/ml. The results represent fold stimulation of $^3$H-thymidine incorporation in the indicated assay cell in the presence (+) or absence (−) of heparin. Each value represents the mean result from two independent experiments in which each point, in turn, represents the mean value of duplicate analyses.

Production of anti-KGF antibodies. Several kinds of antibodies which recognize KGF or KGF-like polypeptides have been prepared using standard methodologies well known in the art of experimental immunology and summarized in the Methods section, above. These include: monoclonal antibodies raised in mice against intact, purified protein from human fibroblasts; polyclonal antibodies raised in rabbits against synthetic peptides with sequences based on amino acid sequences predicted from the KGF cDNA sequence; polyclonal antibodies raised in rabbits against both naturally secreted KFG from human fibroblasts and recombinant KGF produced in *E. coli* (see next section).

Monoclonal antibodies from three different hybridomas have been purified. All three recognize the recombinant as well as the naturally occurring KGF in a solid-phase (ELISA) assay. None cross-reacts with KGF under denaturing conditions (in a Western blot), and none neutralizes mitogenic activity of KGF in the BALB/MK bioassay.

Polyclonal antibodies were generated with a synthetic peptide with the amino acid sequence NDMTPEQMATNVR, corresponding to residues numbered 32 through 44 in KGF (see FIG. 7), plus an R (Arg) residue instead of the actual Asn residue encoded by the cDNA at position 45. The Asn residue is probably glycosylated in the natural KGF polypeptide and, therefore, was not identified in the amino acid sequencing data obtained directly from that polypeptide (see Discussion, below). Polyclonal antibodies generated with this synthetic peptide recognize both naturally occurring and recombinant KGF in ELISA and Western blot analyses at a level of sensitivity of at least as low as 10 ng protein. These antibodies, however, do not neutralize mitogenic activity of KGF in the BALB/MK bioassay.

Polyclonal antisera against intact natural KGF protein recognizes KGF in both ELISA and Western blot assays. Such antibodies also appear to inhibit mitogenic activity of KGF in the BALB/MK bioassay.

Expression of KGF cDNA in *E. coli*. KGF cDNA was expressed to produce polypeptide, in *E. coli* by placing its coding sequence under control of the hybrid trk promoter (comprising elements of trp and lac promoters), in the plasmid pKK233-2 (Amman, E. and Brosius, J. (1985) Gene 40, 183). To accomplish this, a specific length of KGF cDNA that contained the information to code for the mature KGF molecule (i.e., without its signal peptide) was amplified using the polymerase chain reaction technique (Sakai, R. K., Scharf, S., Faloona, F., Mullis, K. B., Norn, G. T., Erlich, H. A. and Arnheim, N. (1985) Science 230, 1350–1354). The fragment was directionally inserted between two sites in the vector, namely the NcoI site, made blut ended by S1 nuclease digestion, and the HindIII site, using standard recombinant DNA methodology. Selected recombinants were sequenced at their cDNA 5' ends to ensure correct alignment of the ATG initiation codon with the regulatory elements of the trk promoter.

Several recombinants were tested for protein production by the usual small scale methods. In brief, the clones were grown to mid-exponential phase ($OD_{595}$ ~0.5), treated with 1 mM isopropyl β-D-thiogalactopyranoside (IPTG) for 90 minutes, and cell extracts were run on SDS-polyacrylamide gels for Western blot analysis. All recombinants tested synthesized a protein that was recognized by antibodies raised against an amino-terminal KGF peptide. One recombinant was selected which showed the greatest induction from IPTG, for further protein analyses.

One liter of bacteria was grown up in NZY broth containing 50 μg/ml ampicillin and 12.5 μg/ml tetracycline, to $OD_{595}$ ~0.5, and treated for 90 min. with IPTG. The cells were collected by centrifugation, resuspended in 50 mM sodium phosphate (pH 7.3), 0.2 M NaCl, and lysed by sonication. Cell debris was removed by centrifugation, and lysate applied directly to a heparin-Sepharose affinity column.

As determined by Western blot analysis and mitogenic activity in keratinocytes, recombinant KGF was eluted in 0.5–0.6 M NaCl. Subsequent purification of the HSAC material with a Mono-S (FPLC) column (Pharmacia) yielded a preparation of KGF estimated to be ≧90% pure, as judged by electrophoretic analysis using SDS-polyacrylamide gels and silver-staining.

Recombinant KGF efficiently stimulated thymidine incorporation into BALB/MK keratinocyte cells, but was only marginally active on NIH/3T3 fibroblasts. Half-maximal stimulation of the BALB/MK cells in the standard keratinocyte bioassay was achieved with a concentration of between 2 to 5 ng/ml, compared to a concentration of 10 to 15 ng/ml for KGF purified from M426 cells. One liter of bacterial cells yielded approximately 50 μg of Mono-S purified recombinant KGF.

Construction of a chimera containing KGF and aFGF sequences. The studies above indicated that KGF possessed two distinctive characteristics which might be encoded by distinct portions or domains of the polypeptide sequence, as is well known to occur in coding sequences of other multifunctional polypeptides. To test this possibility, a chimeric DNA segment encoding the $NH_2$-terminal sequence of KGF grafted onto the C-terminal core of the aFGF was constructed, as follows. A Sau3AI restriction enzyme site (GATC) in the 5' end of the KGF cDNA, within codons for residues 76, 77, and 78 (Tyr, Leu, and Arg, respectively; see FIG. 7) was cut and joined to an homologous site in the aFGF cDNA within codons for amino acids 39 (Arg) and 40. The 3' and 5' ends of this chimeric DNA were joined to the vector DNA of the plasmid pKK233-2 by the same method used for insertion of the KGF cDNA encoding the secreted form of polypeptide (see Methods, above).

When recombinant *E. coli* cells were constructed using the vector carrying the chimera, and expression tests were conducted as described for mature KGF, above, a novel product with properties of both KGF and aFGF was produced. The peptide was enriched by heparin-Sepharose chromatography and found to have a target cell preference for keratinocytes, like KGF, with minimal activity on fibroblasts (NIH/3T3). The mitogenic activity of this chimeric polypeptide lacks, however, susceptibility to inhibition of heparin, a characteristic which parallels that of aFGF rather than KGF. In fact, the mitogenic activity on keratinocytes is actually enhanced by heparin, as is the case for aFGF. Thus the peptide domains responsible for target cell specificity and heparin sensitivity are clearly distinct and readily separable in KGF, according to the practice of the present invention.

DISCUSSION

The experiments described in this section illustrate the practice of several principal embodiments of the present invention. These include isolation of cDNAs encoding KGF, expression of such cDNAs in recombinant cells, production of various antibodies reactive with KGF, and construction and expression of a chimeric cDNA encoding a novel growth factor with amino acid sequences and related functionalities of both KGF and aFGF. The following points related to these embodiments may also be noted to enhance the understanding of the present invention.

The sequence predicted from the KGF cDNA agreed with the amino acid sequence determined from the purified KGF form secreted by human fibroblasts. Moreover, the sequence offered potential explanations for positions where definitive amino acid assignments could not be made by direct amino acid sequencing. Residues 32 and 46 are predicted from the cDNA sequence to be cysteines, and hydrolyzed derivatives of unmodified cysteine residues are not detectable following Edman degradation. The predicted KGF amino acid sequence also contained one potential N-linked glycosylation site (Asn-X-Ser/Thr) from residues 45 through 47. If Asn 45 were glycosylated, it would not be detected by the amino acid sequencing methods employed here. In fact, KGF migrates as a broad band on NaDodSO$_4$/PAGE at a higher molecular weight than predicted for the purified protein. This may be accounted for by glycosylation.

The FGFs are heparin-binding mitogens with broad target cell specificities (Thomas, K. (1987) *FASEB J*. 1, 434–440). The hst gene was identified as a transforming gene from a human stomach tumor (Taira et al., *Proc. Natl. Acad. Sci. USA* 84: 2980–2984 (1987), adjacent normal stomach tissue (Yoshida et al., *Proc. Natl. Acad. Sci. USA* 84: 7305–7309 (1987), and from Kaposi's sarcoma (Delli-Bovi et al., *Proc. Natl. Acad. Sci. USA* 84: 5660–5664 (1987), by standard NIH/3T3 transfection assays. The product of the int-2 gene is expressed normally during mouse embryogenesis (Jakobovits, A., Shackleford, G. M., Varmus, H. E. and Martin, G. R. (1986) *Proc. Nat. Acad. Sci. USA* 83, 7806–7810) and aberrantly after proviral integration of mouse mammary tumor virus (Peters, G., Brookes, S. and Dickson, S. (1983) *Cell* 33, 364–377).

KGF is the sixth member of the fibroblast growth factor family to be identified (Zhan, X., Bates, B., Hu, X. and Goldfarb, M. (1988) *Mol. Cell. Biol.* 8, 3487–3495). While the name FGF-6 does not seem suitable because KGF is devoid of activity on fibroblasts, this nomenclature may also be used for this growth factor, to denote its structural relationship to the FGF family. As all previously characterized growth factors either exclude epithelial cells as targets or include them among a number of sensitive target cells, the highly specific nature of KGF mitogenic activity for epithelial cells, and the sensitivity of keratinocytes in particular, make it unique.

In studies to date, expression of the KGF transcript appears to be specific for stromal cells derived from epithelial tissues, suggesting its function in normal epithelial cell proliferation. The availability of the KGF cDNA clone will make it possible to determine whether abnormal expression of this growth factor can be implicated in clinical conditions characterized by epithelial cell dysplasia and/or neoplasia. Moreover, the ability to produce large quantities of this novel growth factor by recombinant techniques should allow testing of its clinical applicability in situations where specific growth of epithelial cells is of particular importance.

Figure 9:
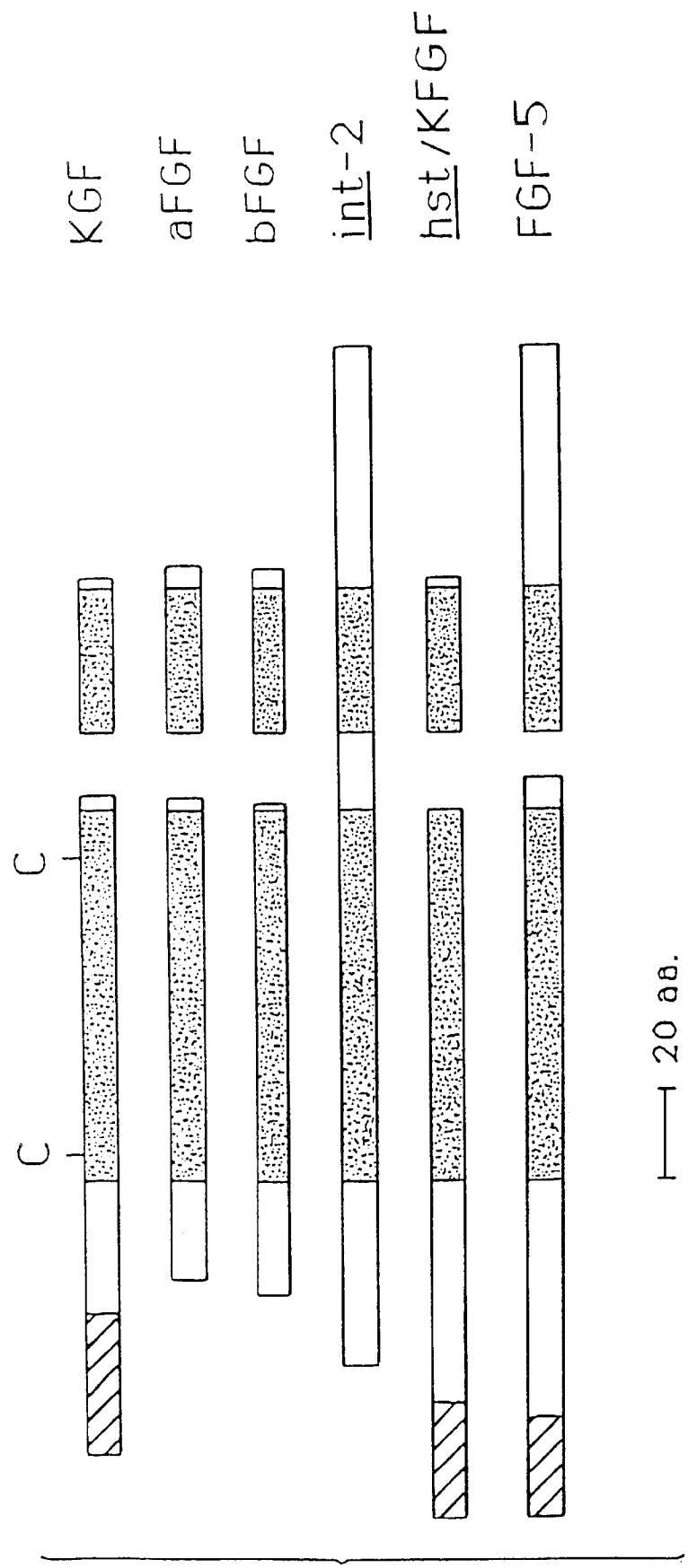
FIG. 9 illustrates the topological comparison of the FGF family of related molecules, including KGF, with emphasis on the two protein domains that share high homology (shaded boxes), the putative signal peptide sequences (hatched boxes), and the two conserved cysteine residues (positions labeled with a "C").

Alignment of the KGF sequence with the five other proteins of the FGF family revealed two major regions of homology, spanning amino acids 65–156 and 162–189 in the predicted KGF sequence, which were separated by a short, nonhomologous series of amino acids with varying lengths in different members of the family (FIG. 9). In the case of int-2, the length of this sequence was 17 residues, while in hst, the two homologous regions were contiguous. In KGF the intervening sequence consisted of five amino acids.

In the aligned regions, the KGF amino acid sequence was about 44% identical to int-2 (mouse), 41% identical to FGF-5 (human), 39% identical to bFGF (human), 37% identical to aFGF (human) and 33% identical to hst (human). In this same region, all six proteins were identical at 19% of the residues, and allowing for conservative substitutions, they showed 28% homology.

As shown in FIG. 9, the amino terminal of these related proteins are nonhomologous and of variable length. The primary KGF and hst translation products contain hydrophobic N-terminal regions which likely serve as signal sequences (von Heijne, G. (1986) *Nucl. Acids Res.* 14, 4683–4690). The fact that this N-terminal domain is not present in the mature KGF molecule (FIG. 7) further supports this conclusion. In contrast, the FGFs are synthesized apparently without signal peptides (Thomas, K. (1987) *FASEB J*. 1, 434–440). The int-2 protein contains an atypically short region of N-terminal hydrophobic residues (von Heijne, G. (1986) *Nucl. Acids Res.* 14, 4683–4690), but it is not known if the protein is secreted. Moreover, the int-2 protein contains a long C-terminal extension compared to the other family members.

Purified KGF contains five cysteine residues, two of which are conserved throughout the family of FGF related proteins (FIG. 9). Also of note are the five pairs of basic residues throughout the KGF sequence. This same pattern has been observed in other FGF family members and may be involved in their interaction with heparin (Schwarzbauer, J. E., Tamkum, J. M., Lemischka, I. R. and Hynes, R. O. (1983) *Cell* 35, 421–431). Dibasic sites are also common targets for proteolytic processing and such processing might account for the microheterogeneity observed in some KGF preparations (unpublished data).

The KGF cDNA sequence was AT rich throughout its length, but particularly so in the 3' untranslated region where the AT content was 70% as compared to 60% in the putative coding sequence and 63% in the 5' untranslated region. The 3' untranslated region contained a large number of ATTTA sequences, which have been proposed to be involved in the selected degradation of transiently expressed, unstable RNAs (Shaw, G. and Kamen, R. (1986) *Cell* 46, 659–667).

There was no classical AATAAA polyadenylation signal but two variant sequences, AATTAA and AATACA (Birnsteil, M. L., Busslinger, M. and Strub, K. (1985) *Cell* 41, 349–359), were detected 24 and 19 nucleotides, respectively, upstream of the poly(A) sequence at the 3' end of the cDNA.

It has been suggested that the heparin effect on acidic FGF is either due to stabilization of the active conformation of the growth factor or to formation of a tertiary complex with acidic FGF and its receptor (Schrieber, A. B., Kenny, J., Kowalski, W., Friesel, J., Mehlman, T. and Maciag, T. (1985) *Proc. Natl. Acad. Sci. USA* 82, 6138–6142, Gospodarowicz, O. and Cheng, J. (1986) *J. Cell. Physiol.* 128, 475–485). If so, heparin may stabilize a conformation of KGF that is not as active as the free molecule, or form a tight complex that is unable to efficiently interact with its receptor.

While its ability to bind heparin reflects the structural similarities of KGF with the FGF's, the differences in target cell specificities between these related mitogens is remarkable. The FGF's induce division of most nonterminally differentiated cells of both embryonic mesodermal and neuroectodermal origin. In addition to fibroblasts and vascular endothelial tissues, mesodermally derived targets in culture include myoblasts, chondrocytes and osteoblasts (Thomas, K. A. and Giminez-Gallego, G. (1986) *Trends Biochem. Soc.* 11, 81–84). FGF's are also mitogenic for glial astrocytes and neuroblasts (Gensburger, C., Labourdette, G. and Sensembrenner, M. (1987) *FEBS Lett.* 217, 1–5). The product of the oncogene isolated from Kaposi's sarcoma, which is identical to hst, also stimulates proliferation of NIH/3T3 and capillary endothelial cells (Delli-Bovi, P., Curatola, A. M., Kern, F. G., Greco, A., Ittman, M. and Basilico, C. (1987) *Cell* 50, 729–737). To date, KGF induced mitogenesis has only been observed in epithelial cells, and the absence of any detectable activity in fibroblasts or endothelial cells has also been demonstrated (see Experimental Section I, above and Rubin et al., *Proc. Natl. Acad. Sci. USA* 86: 802–806 (1989). It seems likely, therefore, that KGF acts through a different cell surface receptor than the FGFs.

There is no significant N-terminal homology between KGF and other FGF-related proteins. Thus, the construction of chimeric molecules between KGF and a prototype FGF was undertaken to determine whether the KGF N-terminal domain is sufficient to account for its unique target cell specificity. The results on the first such recombinant polypeptide sequence indicate that the N-terminal domain of KGF essentially encodes the cell preference for keratinocytes, while the susceptibility of KGF to heparin is encoded somewhere in the C-terminal core region which was replaced by sequences of aFGF. This novel KGF-like growth factor may have advantages in clinical applications where administration of an epithelial-specific growth factor is desirable in the presence of heparin, a commonly used anticoagulant. Additional studies on chimeras should also provide insights into which specific domains in the C-terminal core contribute the different effects of heparin on their biologic activities.

For purposes of completing the background description and present disclosure, each of the published articles, patents and patent applications heretofore identified in this specification is hereby incorporated by reference into the specification.

The foregoing invention has been described in some detail for purposes of clarity and understanding. It will also be obvious that various combinations in form and detail can be made without departing from the scope of the invention.

What is claimed is:

1. An isolated keratinocyte growth factor (KGF) polypeptide prepared by expressing in a host cell a DNA encoding a polypeptide having a sequence comprising amino acids 32–194 of FIG. 7.

2. The polypeptide of claim 1, wherein said DNA encodes a Met at the amino terminus.

3. The polypeptide of claim 1, wherein said host cell is selected from the group consisting of a bacterial cell, a fungal cell, a mammalian cell and an insect cell.

4. The polypeptide of claim 3, wherein said cell is a bacterial cell.

5. The polypeptide of claim 3, wherein said cell is a mammalian cell.

6. An isolated keratinocyte growth factor (KGF) polypeptide, wherein said polypeptide comprises amino acids 32 to 194 of FIG. 7 or comprises a segment of said polypeptide, wherein said polypeptide and segment thereof has mitogenic activity on BALB/MK cells.

7. The polypeptide or segment thereof of claim 6, which comprises Met at the amino terminus.

8. The polypeptide or segment thereof of claim 6, wherein five nanomolar concentration of said polypeptide or segment thereof elicits less than one-fold stimulation over background in NIH/3T3 cells.

9. The polypeptide or segment thereof of claim 6, wherein said polypeptide or segment thereof is capable of stimulating DNA synthesis in quiescent BALB/MK epidermal keratinocytes at a concentration of 0.1 nM.

10. The polypeptide or segment thereof of claim 6, wherein an amount of said polypeptide that stimulates maximal thymidine incorporation in BALB/MK keratinocyte cells, stimulates less than one-fold stimulation over background in NIH/3T3 fibroblasts.

11. The polypeptide or segment thereof of claim 6, wherein an amount of said polypeptide or segment thereof that stimulates maximal thymidine incorporation in BALB/MK keratinocyte cells, stimulates less than $\frac{1}{50}$th of the maximal thymidine incorporation in NIH/3T3 cells stimulated by aFGF or bFGF.

12. The polypeptide or segment thereof of claim 6, wherein an amount of said polypeptide or segment thereof that stimulates maximal thymidine incorporation in BALB/MK keratinocyte cells, stimulates less than $\frac{1}{10}$th of the maximal thymidine incorporation in NIH/3T3 fibroblasts stimulated by EGF or TGF-alpha.

13. The polypeptide or segment thereof of claim 6, wherein the maximal thymidine incorporation in BALB/MK keratinocytes stimulated by said polypeptide or segment thereof obtained within the concentration range of 0.1 to 3 nanomolar is at least twice that obtained with bFGF within the same concentration range.

14. An isolated keratinocyte growth factor (KGF) polypeptide, wherein said polypeptide comprises the amino acids 32–194 of FIG. 7 or comprises a segment of said polypeptide which is that part of the amino acid sequence of FIG. 7 that remains after the amino acid sequence of FIG. 7 is truncated from an N terminus to C terminus direction, while the region of amino acids 32–78.

15. The polypeptide or segment thereof of claim 14, which comprises Met at the amino terminus.

16. The polypeptide of claim 14 or segment thereof, which has mitogenic activity on BALB/MK keratinocyte cells.

17. The polypeptide or segment thereof of claim 14, which has mitogenic activity on epithelial cells.

18. An isolated keratinocyte growth factor (KGF) polypeptide, wherein said polypeptide comprises amino acids 32–194 of FIG. 7 or comprises a segment of said polypeptide which is that part of the amino acid sequence of FIG. 7 that remains after the amino acid sequence of FIG. 7 is truncated from the C terminus toward the N terminus, within the region of amino acids 194 to 189.

19. The polypeptide or segment thereof of claim 18, which comprises Met at the amino terminus.

20. The polypeptide or segment thereof of claim 18, which has mitogenic activity on BALB/MK keratinocyte cells.

21. The polypeptide or segment thereof of claim 18, which has mitogenic activity on epithelial cells.

22. An isolated keratinocyte growth factor (KGF) polypeptide, wherein said polypeptide comprises amino acids 32–194 of FIG. 7 or comprises a segment of said polypeptide which is that part of the amino acid sequence of FIG. 7 that remains after the amino acid sequences of FIG. 7 is truncated from an N terminus to C terminus direction, within the region of amino acids 32–78 and is truncated from the C terminus toward the N terminus, within the region of amino acids 194 to 189.

23. The polypeptide or segment thereof of claim 22, which comprises Met at the amino terminus.

24. The polypeptide or segment thereof of claim 22, which has mitogenic activity on BALB/MK keratinocyte cells.

25. The polypeptide or segment thereof of claim 22, which has mitogenic activity on epithelial cells.

26. An isolated keratinocyte growth factor (KGF) polypeptide, wherein said polypeptide comprises amino acids 32–194 of FIG. 7.

27. The polypeptide of claim 26, which comprises Met at the amino terminus.

28. An isolated keratinocyte growth factor (KGF) polypeptide prepared by expressing in a host cell a DNA encoding an amino acid sequence comprising amino acids 32–194 of FIG. 7 or encoding an amino acid sequence which is a segment of amino acids 32–194 of FIG. 7, wherein the segment is that part of the amino acid sequence of FIG. 7 that remains after the amino acid sequence of FIG. 7 is truncated from an N terminus to C terminus direction, within the region of amino acids 32–78.

29. The polypeptide or segment thereof of claim 28, wherein said DNA encodes Met at the amino terminus.

30. The polypeptide or segment thereof of claim 28, which has mitogenic activity on BALB/MK keratinocyte cells.

31. The polypeptide or segment thereof of claim 28, which has mitogenic activity on epithelial cells.

32. An isolated keratinocyte growth factor (KGF) polypeptide, wherein said polypeptide comprises amino acids 32 to 194 of FIG. 7 or comprises a segment of said polypeptide, and wherein said polypeptide and segment thereof has mitogenic activity on epithelial cells.

33. The polypeptide or segment thereof of claim 32, which comprises Met at the amino terminus.

34. The polypeptide of claim 32, that is a segment of the polypeptide of FIG. 7.

35. The polypeptide or segment thereof of claim 32, wherein five nanomolar concentration of said polypeptide or segment thereof elicits less than one-fold stimulation over background in NIH/3T3 cells.

36. The polypeptide or segment thereof of claim 32, wherein said KGF is capable of stimulating DNA synthesis in quiescent BALB/MK epidermal keratinocytes at a concentration of 0.1 nM.

37. The polypeptide or segment thereof of claim 32, wherein an amount of said polypeptide or segment thereof that stimulates maximal thymidine incorporation in BALB/MK keratinocyte cells, stimulates less than one-fold stimulation over background in NIH/3T3 fibroblasts.

38. The polypeptide or segment thereof of claim 32, wherein an amount of said polypeptide or segment thereof that stimulates maximal thymidine incorporation in a BALB/MK keratinocyte cells, stimulates less than 1/50'th of the maximal thymidine incorporation in NIH/3T3 cells stimulated by aFGF or bFGF.

39. The polypeptide or segment thereof of claim 32, wherein an amount of said polypeptide or segment thereof that stimulates maximal thymidine incorporation in BALB/MK keratinocyte cells, stimulated less than 1/10th of the maximal thymidine incorporation in NIH/3T3 fibroblasts stimulated by EGF or TGF-alpha.

40. The polypeptide or segment thereof of claim 32, wherein the maximal thymidine incorporation in BALB/MK keratinocytes stimulated by said polypeptide or segment thereof obtained within the concentration range of 0.1 to 3 nanomolar is at least twice that obtained with bFGF within the same concentration range.

41. An isolated keratinocyte growth factor (KGF) polypeptide comprising a segment of amino acids 32–194 of FIG. 7, wherein said polypeptide and segment thereof has mitogenic activity on epithelial cells and wherein said polypeptide is unglycosylated.

42. An isolated keratinocyte growth factor (KGF) polypeptide comprising a segment of amino acids 32–194 of FIG. 7, wherein the segment is that part of the amino acid sequence of FIG. 7 that remains after the amino acid sequence of FIG. 7 is truncated from an N terminus to C terminus direction, within the region of amino acids 32–78, and wherein said polypeptide is unglycosylated.

43. The polypeptide or segment thereof of any of claims 1 to 40, wherein said polypeptide or segment thereof is unglycosylated.

44. The polypeptide or segment thereof of any of claims 1 to 40, wherein said polypeptide or segment thereof is glycosylated.

* * * * *

UNITED STATES PATENT AND TRADEMARK OFFICE
CERTIFICATE OF CORRECTION

PATENT NO. : 6,420,531 B1
DATED : July 16, 2002
INVENTOR(S) : Rubin et al.

It is certified that error appears in the above-identified patent and that said Letters Patent is hereby corrected as shown below:

Column 28,
Line 58, change "while" to -- within --.

Column 29,
Line 17, change "sequences" to -- sequence --.

Column 30,
Line 20, delete "a".
Line 21, delete """ between "1/50" and "th".
Line 27, change "stimulated" to -- stimulates --.

Signed and Sealed this

Fourth Day of May, 2004

JON W. DUDAS
*Acting Director of the United States Patent and Trademark Office*